United States Patent
Feinberg et al.

(10) Patent No.: US 10,022,179 B2
(45) Date of Patent: Jul. 17, 2018

(54) BIPOLAR MEDICAL DEVICES FOR EXTRACTING TISSUE AND METHODS THEREFOR

(75) Inventors: Marc Feinberg, Ringoes, NJ (US); Mosaddeq Hossain, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 1078 days.

(21) Appl. No.: 12/967,686

(22) Filed: Dec. 14, 2010

(65) Prior Publication Data
US 2012/0150179 A1   Jun. 14, 2012

(51) Int. Cl.
*A61B 18/14* (2006.01)
*A61B 18/00* (2006.01)

(52) U.S. Cl.
CPC ............. *A61B 18/1445* (2013.01); *A61B 2018/00035* (2013.01); *A61B 2018/00196* (2013.01); *A61B 2018/00202* (2013.01); *A61B 2018/00208* (2013.01); *A61B 2018/00547* (2013.01); *A61B 2018/00589* (2013.01); *A61B 2018/00595* (2013.01); *A61B 2018/00601* (2013.01)

(58) Field of Classification Search
CPC ............ A61B 18/1442; A61B 18/1445; A61B 18/1447; A61B 18/145; A61B 2018/145; A61B 2018/1452; A61B 2018/1457
USPC ...... 606/45, 51, 52, 170, 179, 180, 205–207
See application file for complete search history.

(56) References Cited

U.S. PATENT DOCUMENTS

| | | | | |
|---|---|---|---|---|
| 3,906,954 A | * | 9/1975 | Baehr et al. | 606/107 |
| 3,989,033 A | * | 11/1976 | Halpern | A61B 10/04 600/567 |
| 5,258,006 A | * | 11/1993 | Rydell | A61B 18/1442 606/205 |
| 5,304,124 A | | 4/1994 | Essig et al. | |
| 5,352,223 A | * | 10/1994 | McBrayer | A61B 17/2909 606/205 |
| 5,439,474 A | | 8/1995 | Li | |
| 5,443,472 A | | 8/1995 | Li | |
| 5,458,598 A | | 10/1995 | Feinberg et al. | |

(Continued)

FOREIGN PATENT DOCUMENTS

| | | |
|---|---|---|
| GB | 2436065 | 9/2007 |
| GB | 2441502 | 3/2008 |
| WO | 2005112806 | 12/2005 |

*Primary Examiner* — Ronald Hupczey, Jr.
(74) *Attorney, Agent, or Firm* — Doherty IP Law Group LLC

(57) ABSTRACT

A bipolar medical device for extracting tissue including a handle, and an outer tube projecting from the handle, the outer tube extending along a longitudinal axis and including a proximal end connected with the housing and a distal end spaced from the proximal end. The medical device includes a split tube disposed within the outer tube, the split tube having a distal end including a first cutting element and an opposing second cutting element, a motor coupled with the split tube for selectively rotating the split tube and the first and second cutting elements about the longitudinal axis, and an electrosurgical generator coupled with the split tube, whereby the first cutting element is connectable with a first pole of the electrosurgical generator and the second element is connectable with a second pole of the electrosurgical generator for passing electrical current between the first and second cutting elements.

24 Claims, 27 Drawing Sheets

(56) References Cited

U.S. PATENT DOCUMENTS

| | | | |
|---|---|---|---|
| 5,482,054 A * | 1/1996 | Slater | A61M 1/0043 |
| | | | 600/564 |
| 5,520,634 A | 5/1996 | Fox et al. | |
| 5,562,694 A | 10/1996 | Sauer et al. | |
| 5,626,578 A * | 5/1997 | Tihon | A61B 18/1442 |
| | | | 606/48 |
| 5,879,358 A | 3/1999 | Semm | |
| 5,957,884 A | 9/1999 | Hooven | |
| 6,001,118 A * | 12/1999 | Daniel et al. | 606/200 |
| 6,007,512 A | 12/1999 | Hooven | |
| 6,036,681 A | 3/2000 | Hooven | |
| 6,039,748 A | 3/2000 | Savage et al. | |
| 6,193,715 B1 | 2/2001 | Wrublewski et al. | |
| 6,468,228 B1 | 10/2002 | Topel et al. | |
| 6,663,628 B2 * | 12/2003 | Peters | 606/45 |
| 7,232,439 B2 | 6/2007 | Ciarrocca | |
| 8,012,153 B2 * | 9/2011 | Woloszko et al. | 606/48 |
| 8,162,964 B2 * | 4/2012 | Piippo et al. | 606/159 |
| 8,449,478 B2 * | 5/2013 | Lee | A61B 10/0266 |
| | | | 600/567 |
| 2008/0058846 A1 | 3/2008 | Vosough | |
| 2008/0065021 A1 | 3/2008 | Jenkins et al. | |
| 2008/0065129 A1 | 3/2008 | Batchelor et al. | |
| 2010/0324446 A1 * | 12/2010 | Pendleton | 600/565 |

* cited by examiner

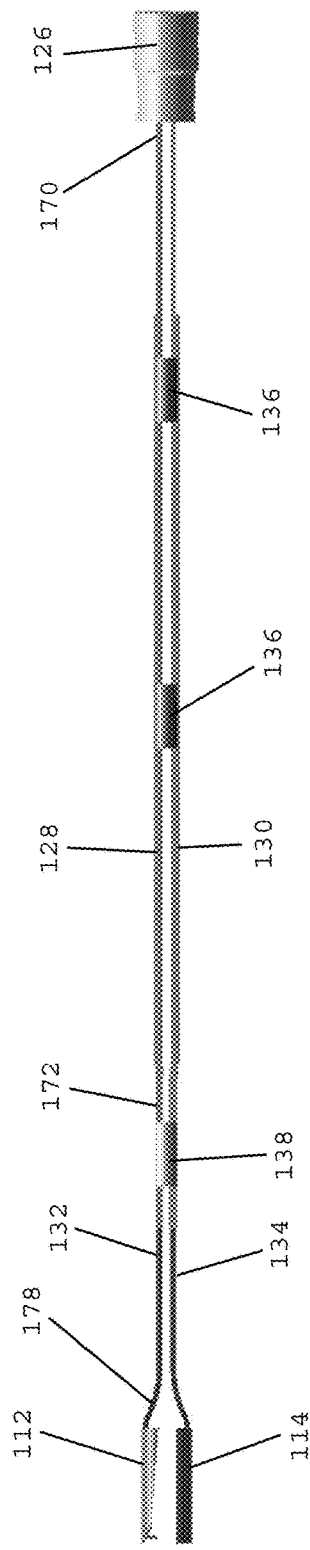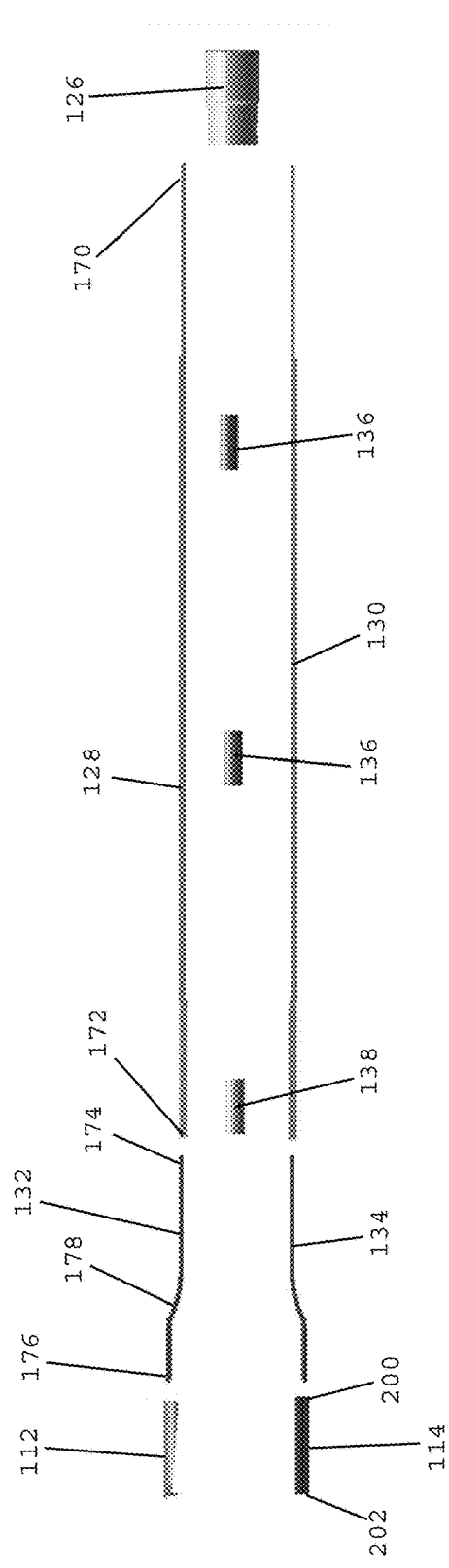
FIG. 4A
FIG. 4B

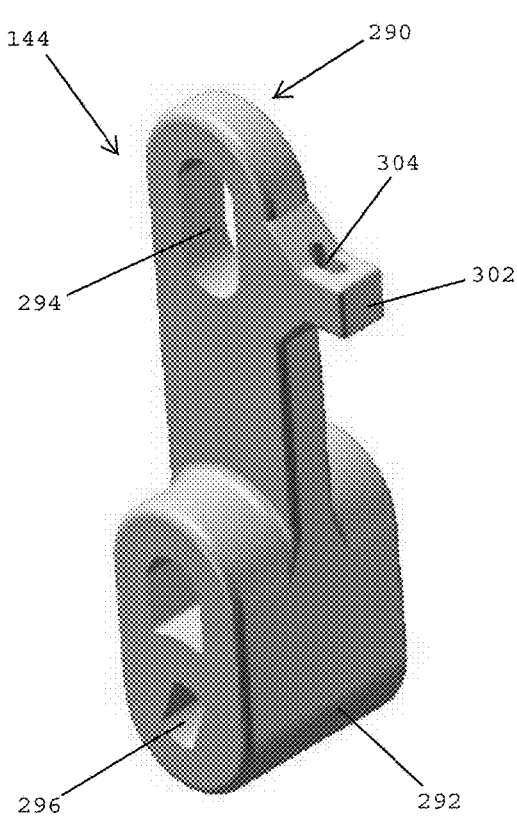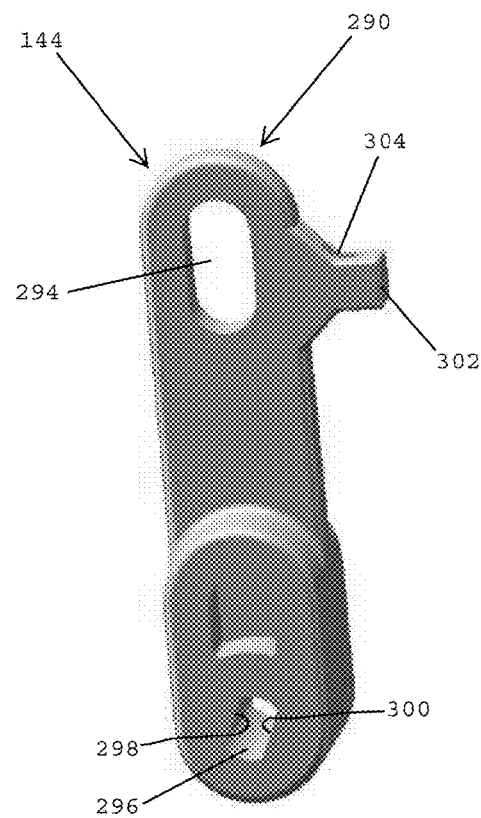
FIG. 14A    FIG. 14B
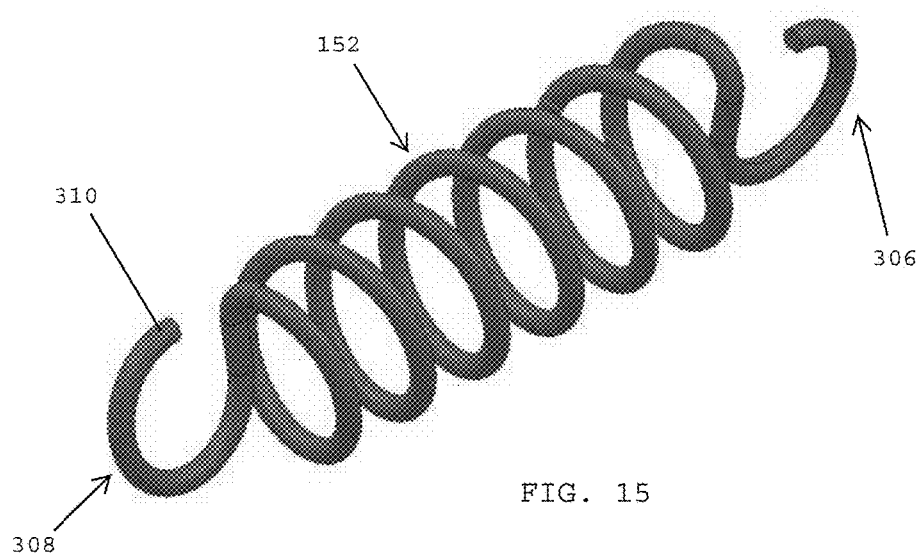
FIG. 15

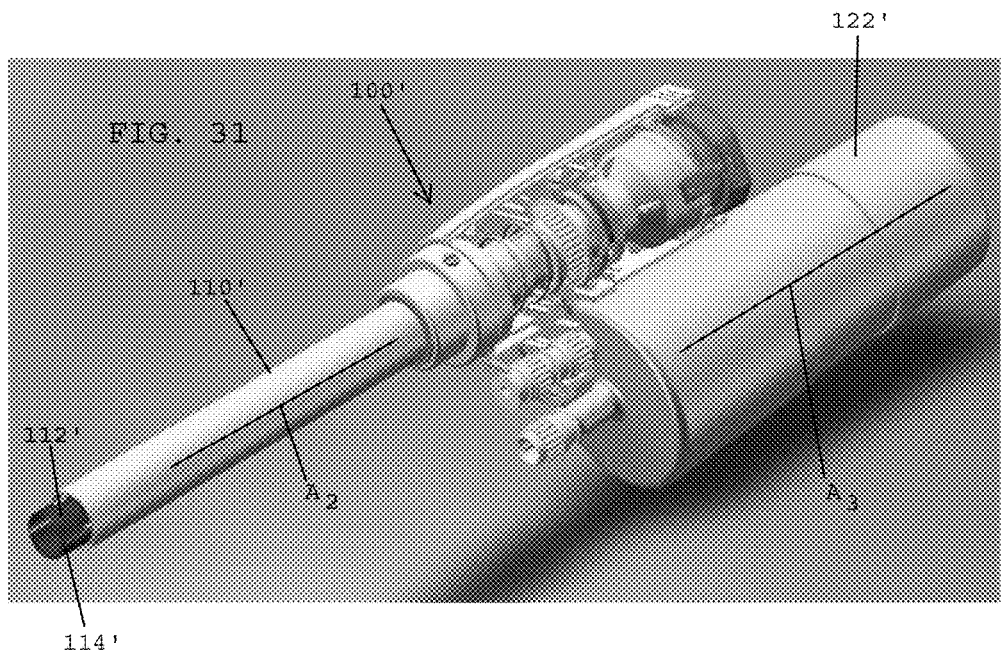
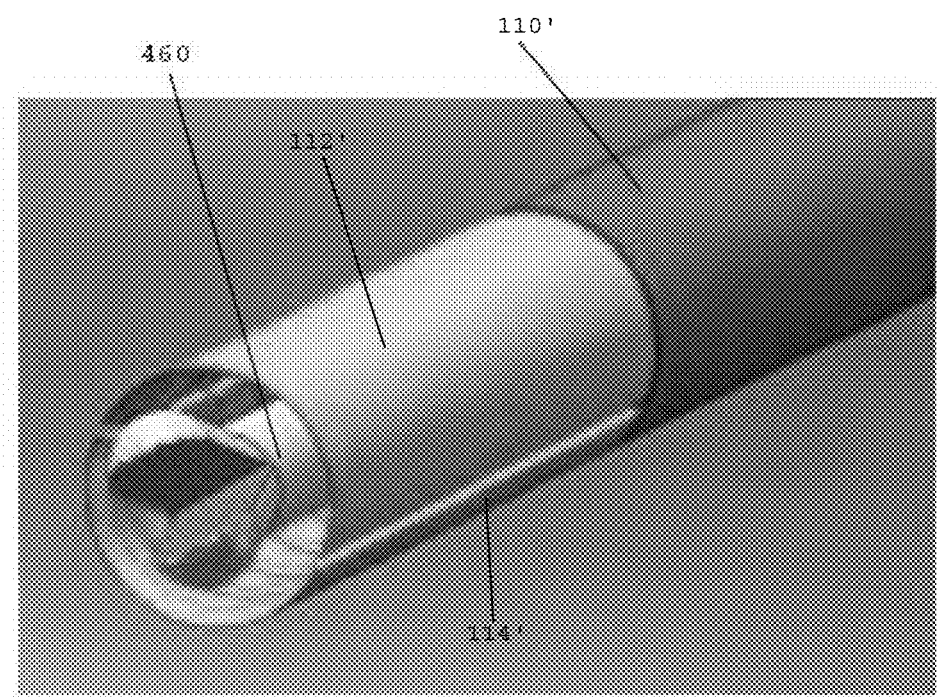
FIG. 32

BIPOLAR MEDICAL DEVICES FOR EXTRACTING TISSUE AND METHODS THEREFOR

BACKGROUND OF THE INVENTION

Field of the Invention

The present invention generally relates to medical devices, and more specifically relates to medical devices used for extracting tissue.

Description of the Related Art

There have been many efforts directed to tissue extraction devices. For example, commonly assigned U.S. Pat. No. 5,458,598 teaches a cutting and coagulating forceps tool having a housing with a protruding barrel, a pair of electrocautery jaws that are closed by camming contact with the mouth of the barrel when the jaws are retracted, and an independently sliding cutting blade that passes between the jaws. The jaws are opened by squeezing a trigger, and the cutting blade is advanced by pressing a lever with the thumb. In use, tissue is grasped between the jaws by first squeezing the trigger to open the jaws, then advancing the jaws over the tissue and releasing the trigger. The torsion spring pulls the jaws back into the mouth of the barrel, whose camming action drives the jaws together, clamping the tissue. Depending upon the thickness of the tissue, the jaws remain partially open a greater or lesser amount. A surgeon may depress a foot pedal to pass a high frequency voltage across the jaws to coagulate the tissue. An electrocauterization procedure destroys tissue using heat conduction from a metal probe that is heated by an electric current. The procedure is used for cutting through soft tissue and to stop bleeding. When the tissue has been sufficiently coagulated, the foot pedal is released, and the blade is advanced by pressing one of the thumb levers forward. When the thumb lever is released, the tension spring retracts the blade, and the tissue is released by squeezing the trigger.

Commonly assigned U.S. Pat. No. 5,520,634 discloses a mechanical morcellator that provides for the removal of tissue without requiring large entry incisions. The mechanical morcellator is adapted to be inserted through a laparoscopic port site and directly fragment and aspirate tissue from within a patient's body. The mechanical morcellator includes a rotatable and retractable cutting head. User manipulation varies the amount the cutting head extends out of a sheath, the amount of suction communicated to the cutting head, and the operation of a motor which rotatably drives the cutting head. Suction is communicated to the cutting head to aspirate the tissue fragmented by the cutting head.

Tissue extraction is often necessary to treat Benign prostatic hyperplasia (BPH), which is a condition involving an increase in the size of the prostate in middle-aged and elderly men. BPH is characterized by hyperplasia of prostatic stromal and epithelial cells, resulting in the formation of large, fairly discrete nodules in the periurethral region of the prostate. When sufficiently large, the nodules compress the urethral canal to cause partial, or sometimes complete, obstruction of the urethra, which interferes with the normal flow of urine. BPH also leads to symptoms of urinary hesitancy, frequent urination, dysuria (painful urination), increased risk of urinary tract infections, and urinary retention.

BPH symptoms generally fall into two categories: storage and voiding. Storage symptoms include urinary frequency, urgency (compelling need to void that cannot be deferred), urgency incontinence, and voiding at night (nocturia). Voiding symptoms include weak urinary stream, hesitancy (needing to wait for the stream to begin), intermittency (when the stream starts and stops intermittently), straining to void, and dribbling.

If left untreated, BPH symptoms can worsen. Incomplete voiding typically results in stasis of bacteria in the bladder residue and an increased risk of urinary tract infection. Urinary bladder stones may form from the crystallization of salts in the residual urine. Urinary retention is another form of progression. Acute urinary retention is the inability to void, while in chronic urinary retention the residual urinary volume gradually increases, and the bladder distends. Some patients that suffer from chronic urinary retention may eventually progress to renal failure (e.g., obstructive uropathy).

Many therapies have been developed for treating BPH. These therapies are generally broken down into two groups: minimally invasive treatments (thermotherapy) and surgical treatments. Minimally invasive treatments, which rely on the absorption of necrosed tissue over time to alleviate symptoms, include laser (e.g., non-contact, contact, interstitial types), microwave (e.g., TUMT), and thermotherapies (e.g., Prostiva™ RF therapy). Surgical treatments include transurethral resection of the prostate (TURP), holium laser enucleation of the prostate (HoLEP), transurethral incision of the prostate (TUIP), and transurethral ultrasound-guided laser incision of the prostate (TULIP).

Most of the above-described treatments involve a urethral approach whereby a large bore cystoscope is used to visualize and remove benign tissue. The urethral approach is rather invasive and causes an inflammatory response that restricts the flow of urine and results in the need for a catheter. These treatments also have serious side effects such as retrograde ejaculation (up to 90% in some procedures), impotence and bleeding.

The two most common types of office-based therapies for BPH are Transurethral Microwave Thermotherapy (TUMT) and TransUrethral Needle Ablation (TUNA). Both of these procedures involve delivering enough energy to create sufficient heat to cause cell necrosis in the prostate. The goal of the therapies is to cause sufficient necrosis so that the dead tissue is reabsorbed by the body to shrink the prostate and relieve the obstruction of the urethra. These procedures are typically performed with local anesthesia, and the patient returns home the same day. Common problems after TUMT include inability to urinate and having to use a catheter for a week or more. Urinary retention happens in about 8 in 100 men who have this treatment. Other side effects include blood mixed in with the urine or sperm. Sexual problems also occur whereby about one in three men who have the TUMT procedure have problems then they ejaculate or have blood in their semen. The TUNA procedure is less effective than traditional prostate surgery (e.g., TURP). Side effects include blood in the urine for several days after the procedure, painful urination, or the need for a catheter after surgery.

Transurethral resection of the prostate (TURP) is a broadly used surgical procedure that requires general anesthesia and the insertion of a resectoscope through the urethra and into the prostate. During the TURP procedure, which lasts about 90 minutes, obstructing portions of the prostate are removed using an electric loop. After the TURP procedure is completed, the patient is usually required to stay in the hospital for about one to four days, and use a catheter for about one to three days. Complete recovery takes about four to six weeks. Common side effects include retrograde ejaculation, impotence and bleeding.

During tissue removal procedures, it is desirable to limit the invasiveness of the procedure so as to minimize the trauma experienced by the patient. In modern surgery, access to a surgical site is often provided by using one or more trocars and cannulas that are inserted into tissue. A visualization system is used to identify the target tissue to be removed as well as locate the surgical instruments. However, the entry incision must still be sized to allow for the removal of the severed tissue and, therefore, the reduction in entry incision size is rather limited, even in more or recently developed surgical procedures.

Thus, there remains a need for a minimally invasive benign prostatic hyperplasia device that does not use a transurethral approach to treat BPH. There also remains a need for a minimally invasive medical device for treating BPH that significantly reduces side effect such as retrograde ejaculation, impotence and bleeding. There also remains a need for a minimally invasive medical device for treating BPH that avoids the needs for using a catheter for voiding after the procedure. There also remains a need for a medical device that enables BPH procedures to be performed in an office setting, an ambulatory center, or a surgical suite without requiring hospitalization or an extended hospitalization stay. There also remains a need for a medical device for treating BPH that does not require significant additional capital expenditures. There also remains a need for a BPH medical device that enables for precise core samples of tissue to be removed and that enables the device to reach a target tissue location with less patient trauma. In addition, there is a need for a device used for biopsies that enables tissue samples to be cored and extracted for analysis.

SUMMARY OF THE INVENTION

In one embodiment, a bipolar medical device for extracting tissue preferably includes an outer tube extending along a longitudinal axis, a split tube disposed within the outer tube, the split tube having a distal end including a first cutting element and an opposing second cutting element adapted for rotating about the longitudinal axis for cutting tissue. The medical device desirably includes an electrosurgical generator coupled with the split tube, whereby the first cutting element is connected with a first pole of the electrosurgical generator and the second element is coupled with a second pole the electrosurgical generator. The electrosurgical generator is adapted to generate an electric current that flows between the first and second cutting elements for heating tissue located adjacent the first and second cutting elements.

In one embodiment, the longitudinal axis extends between proximal and distal ends of the outer tube, and the split tube is axially moveable along the longitudinal axis relative to the outer tube. In one embodiment, the split tube is rotatable about the longitudinal axis relative to the outer tube so that the first and second cutting elements are rotatable about the longitudinal axis for cutting tissue.

In one embodiment, a bipolar medical device for extracting tissue desirably includes a handle connected to the proximal end of the outer tube, a motor disposed within the housing and being coupled with the split tube, a power source coupled with the motor, and a motor actuator coupled with the motor for selectively activating the motor for rotating the split tube about the longitudinal axis.

The medical device may also include a lever assembly mounted on the housing and being coupled with the motor and the split tube, whereby the lever assembly is engageable for simultaneously advancing the motor and the split tube toward the distal end of the outer tube. In one embodiment, the medical device has two thumb levers for making the device ambidextrous, however, the device may be modified to provide only one thumb lever. In one embodiment, the motor is preferably slideably mounted within the housing for sliding toward and away from the distal end of the outer tube. In one embodiment, the lever assembly may be engaged for extending the first and second cutting elements from the distal end of the outer tube.

In one embodiment, an electrical current is passed between the first and second cutting elements for cutting, cauterizing, coagulating, desiccating and/or fulgurating tissue. In one embodiment, one or more of the components of the medical device are made of conductive material that are covered with an electrically insulating material, such as a heat shrink electrical insulation material, for preventing electrical contact between one or more of the conductive parts. For example, in one embodiment, the split cutting jaw includes first and second tong extensions that extend between a motor and the first and second cutting elements. The first and second tong extensions are preferable covered with an electrical insulating material for preventing electrical arcing or electrical contact between the tong extensions.

In one embodiment, the first cutting element includes a first semi-tubular body having a concave inner surface, a convex outer surface, and a distal end having at least one sharpened cutting surface, and the second cutting element includes a second semi-tubular body having a concave inner surface that opposes the concave inner surface of the first cutting element and a convex outer surface that faces away from the first cutting element.

In one embodiment, at least one of the first and second cutting elements has a tooth projecting radially inward toward the longitudinal axis. The tooth may be punched-out from one of the first and second cutting elements and is located adjacent a distal end of the one of the first and second cutting elements associated therewith. In one embodiment, the tooth is angled relative to the longitudinal axis so that the tooth includes a leading edge having a sharpened cutting surface that lies within a plane that defines an obtuse angle with the longitudinal axis. During rotation of the first and second cutting elements about the longitudinal axis, the tooth is adapted to cut tissue, and the tooth is adapted to abut against a distal end of the cut tissue for removing the cut tissue from a tissue extraction site.

The medical device disclosed herein may be used for a wide range of tissue extracting, coring and cauterizing procedures including general surgery, gynecology and urology. In one embodiment, the medical device may be used for treating Benign Prostatic Hyperplasia (BPH) by placing the device into contact with the prostate gland via a transperineal approach, which provides many advantages over transurethral approaches. As a result, the present invention significantly reduces side effects such as retrograde ejaculation, impotence and bleeding. The present invention also eliminates the need for a catheter for voiding urine after the procedure. In addition, the present invention enables the procedure to be performed by urologists in an office, ambulatory center or a surgical suite.

In one embodiment, at least one of the cutting elements has a tooth that extends radially inward. The tooth desirably enables precise core samples of tissue to be removed from a patient. In one embodiment, the two cutting elements separate from one another (i.e., open up) after insertion into the tissue and before rotating for enabling the medical device to reach the target tissue with less trauma.

In one embodiment, the medical device disclosed herein may be used with an electrosurgical generator so that there is no new capital equipment required such as laser systems and/or microwave systems.

In one embodiment, a bipolar medical device for extracting tissue preferably includes a handle, an outer tube projecting from the handle, the outer tube extending along a longitudinal axis and including a proximal end connected with the housing and a distal end spaced from the proximal end, a split tube disposed within the outer tube, the split tube having a distal end including a first cutting element and an opposing second cutting element, a motor coupled with the split tube for selectively rotating the split tube and the first and second cutting elements about the longitudinal axis, and an electrosurgical generator coupled with the split tube, whereby the first cutting element is connectable with a first pole of the electrosurgical generator and the second element is connectable with a second pole the electrosurgical generator.

In one embodiment, the motor is desirably adapted to rotate the first and second cutting elements about the longitudinal axis for cutting tissue, and the electrosurgical generator generates an electric current that flows between the first and second cutting elements for heating tissue located adjacent the first and second cutting elements.

In one embodiment, the first and second cutting tubes are preferably extendable from the distal end of the outer tube. The medical device desirably includes a lever assembly coupled with the motor and the split cutting tube for simultaneously advancing the motor and the first and second cutting elements toward the distal end of the outer tube.

In one embodiment, the split tube preferably includes first and second tongs extending through the outer tube and being coupled with a drive shaft of the motor, the first and second tongs being electrically isolated from one another and including respective distal ends that are connected with the first and second cutting elements. The first cutting element desirably has a first semi-tubular body having a concave inner surface, a convex outer surface, and a distal end having at least one sharpened cutting surface, and the second cutting element desirably has a second semi-tubular body having a concave inner surface that opposes the concave inner surface of the first cutting element and a convex outer surface that faces away from the first cutting element.

These and other preferred embodiments of the present invention will be described in more detail below.

BRIEF DESCRIPTION OF THE DRAWING

FIG. 4A shows a front elevational view of a tissue extraction assembly for a bipolar medical device for extracting tissue, in accordance with one embodiment of the present invention.

FIG. 4B shows an exploded view of the tissue extraction assembly of FIG. 4A.

FIGS. 14A and 14B show an actuation lever of a bipolar medical device for extracting tissue, in accordance with one embodiment of the present invention.

FIG. 15 shows an extension spring adapted to be assembled with the actuation lever of FIGS. 14A and 14B.

FIG. 31 shows a perspective view of a bipolar medical device for extracting tissue, in accordance with another embodiment of the present invention.

FIG. 32 shows a distal end of the bipolar medical device shown in FIG. 31 including a tissue grasping tool passed through a central conduit of the device, in accordance with one embodiment of the present invention.

DETAILED DESCRIPTION

Figure 1A:
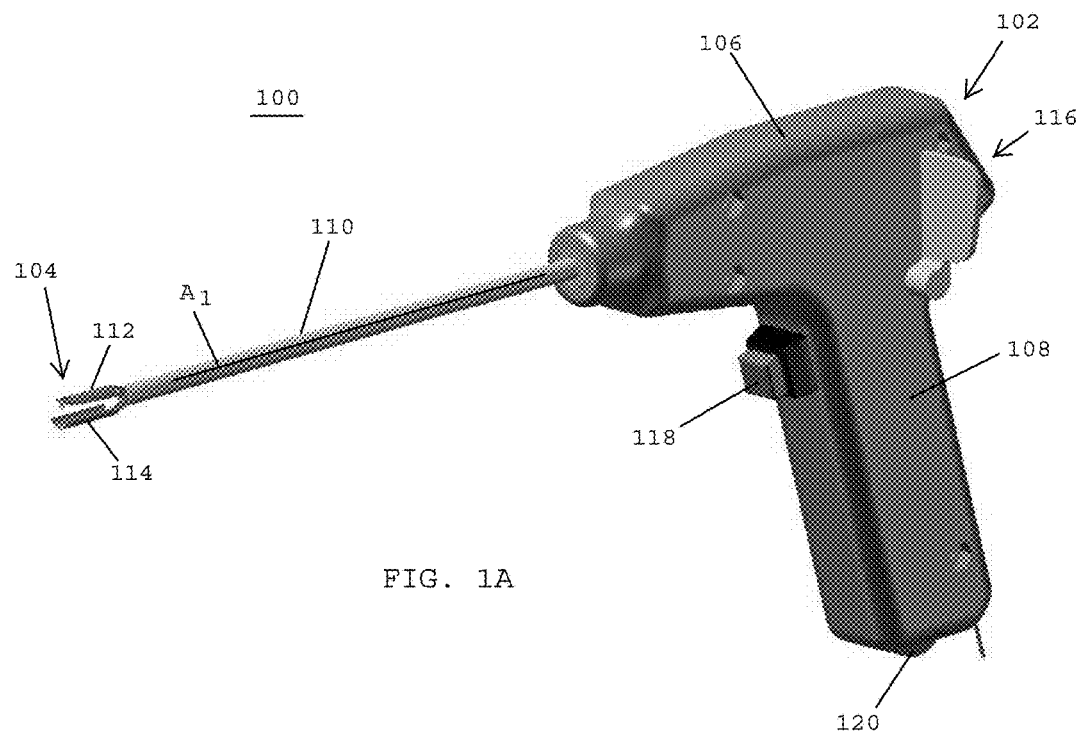
FIG. 1A shows a perspective view of a bipolar medical device for extracting tissue, in accordance with one embodiment of the present invention.
Figure 1B:
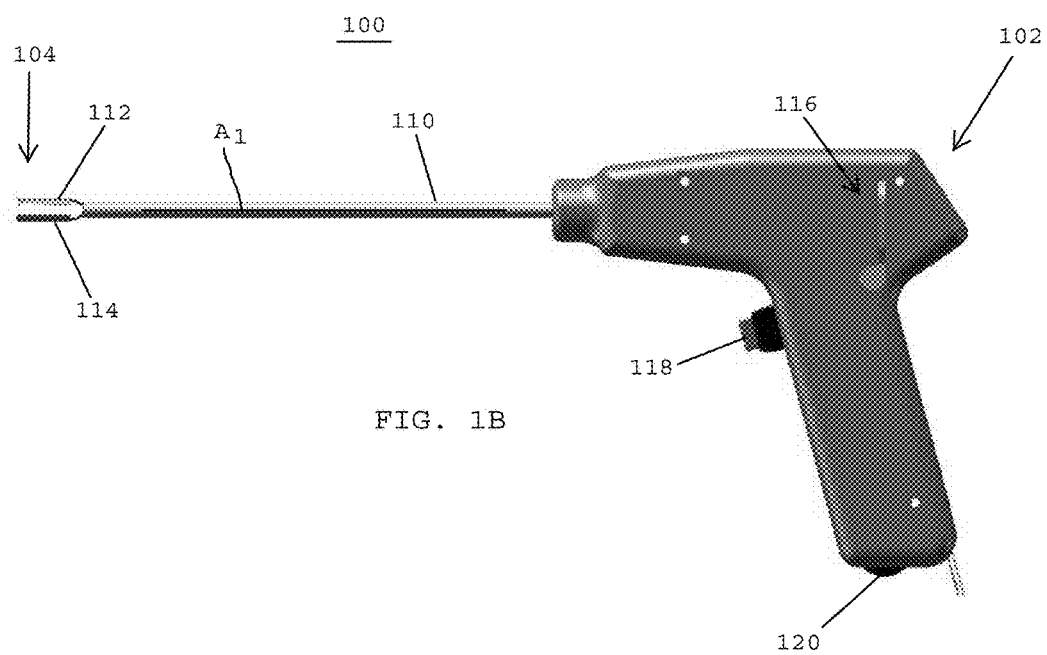
FIG. 1B shows a front elevational view of the bipolar medical device for extracting tissue shown in FIG. 1A.

Referring to FIGS. 1A and 1B, in one embodiment, a bipolar medical device 100 for extracting tissue has a proximal end 102, a distal end 104, and a housing 106 having a hand grip 108. The bipolar medical device 100 desirably includes an outer tube 110, such as a stainless steel outer tube, that projects from a distal end of the housing 106 and extends toward the distal end 104 of the device 100. In one embodiment, the housing 106 may be a molded part such as an injection-molded part. The housing 106 may be made of well-known materials such as ABS and polystyrene. In one embodiment, the housing 106 preferably includes a left housing part and a right housing part that may be assembled together using fasteners, welding, and/or a friction fit.

In one embodiment, the bipolar medical device for extracting tissue disclosed herein may be used for relieving BPH symptoms by removing pressure on the urethra and thereby restoring normal urine flow. Using the device disclosed herein for thermotherapy will desirably cause the body to re-absorb necrosed tissue for further shrinking the prostate, which also relieves any obstruction of the urethra. The present invention minimizes side effects because tissue may be extracted without requiring a large area of thermal destruction as is found in prior art devices.

It is believed that a transperineal approach, as opposed to a urethral approach, results in little or no urethral inflammation and no post-treatment catheterization. In addition, debulking of the prostate relieves pressure on the urethra and may result in immediate BPH relief. The remaining tissue subjected to thermal therapy will be absorbed by the body, further reducing the size of the prostate. In addition, it is believed that the minimally invasive approach disclosed herein avoids serious side effects such as retrograde ejaculation and impotence.

In one embodiment, the bipolar medical device for extracting tissue may be used in conjunction with a standard rectal ultrasound system for visualization of the prostate and positioning of the device. To enhance visualization of the urethra, the bladder may be partially filled using a Foley catheter with water. The catheter may be cool, but not cold, so as to protect the urethra from thermal damage. Since the prostate capsule is pierced in this manner, minimal damage to non-target tissue and minimal side effects are expected.

In one embodiment, the bipolar medical device 100 for extracting tissue desirably includes a tissue extraction assembly that projects from a distal end of the outer tube 110. The tissue extraction assembly preferably includes a split tube having two halves, namely a first cutting element 112 and a second cutting element 114. As will be described in more detail herein, the first and second cutting elements 112, 114 are preferably adapted to rotate about a longitudinal axis $A_1$ for cutting tissue. In one embodiment, the split tube is connected with an electrosurgical generator so that one of the first and second cutting elements 112, 114 is connected to a first pole of the electrosurgical generator and the other one of the first and second cutting elements is connected with an opposite, second pole of the electrosurgical device. The electrosurgical generator is preferably operated for passing an electric current between the first and second cutting elements 112, 114 for heating tissue located between and/or adjacent the first and second cutting elements for halting bleeding of cut tissue. In one embodiment, the electrosurgical device may energize the first cutting element 112 with a positive charge and the second cutting element 114 with a negative charge.

Figure 2:
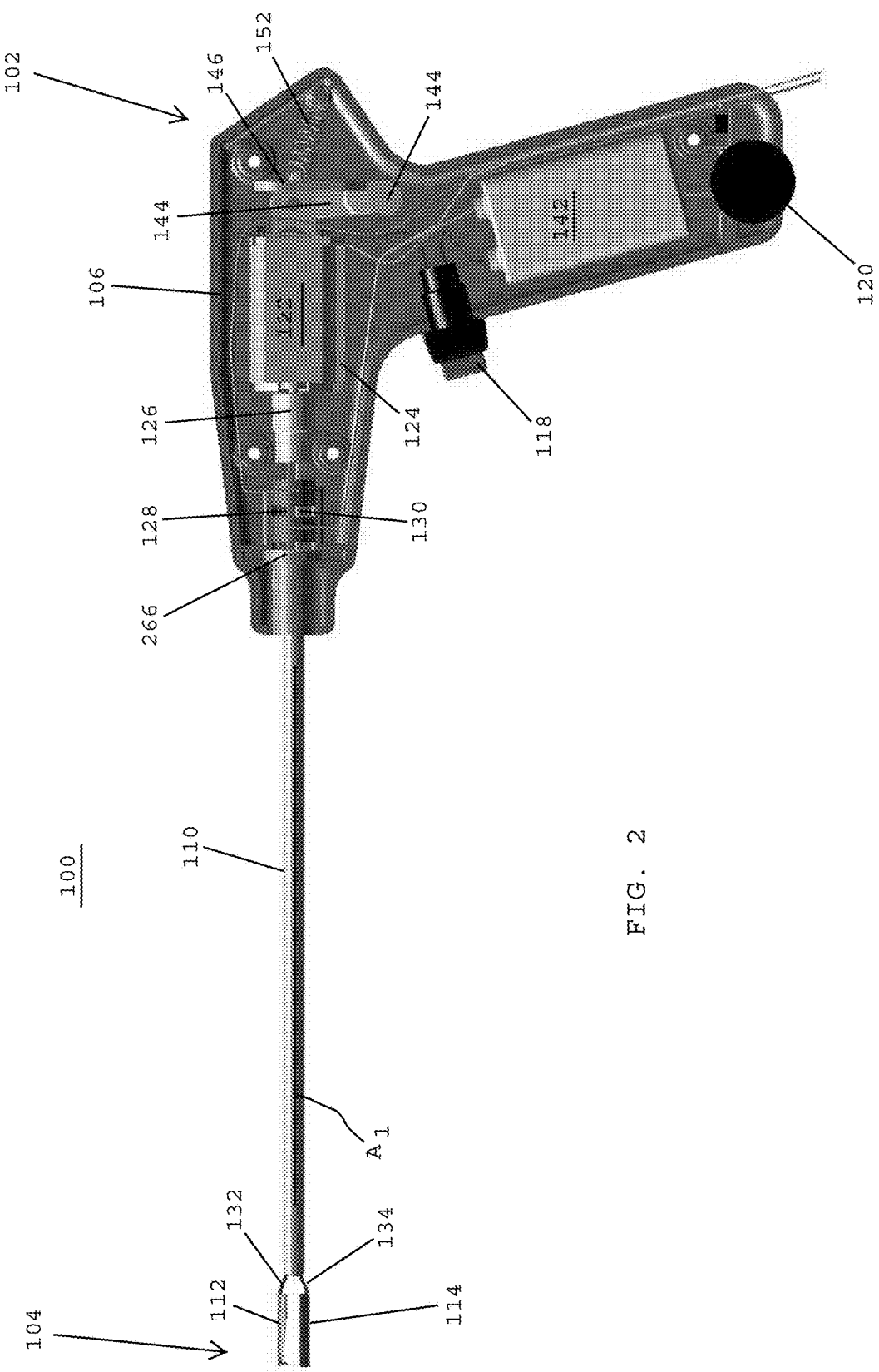
FIG. 2 shows the bipolar medical device for extracting tissue of FIG. 1B with a section of a handle removed.
Figure 3:
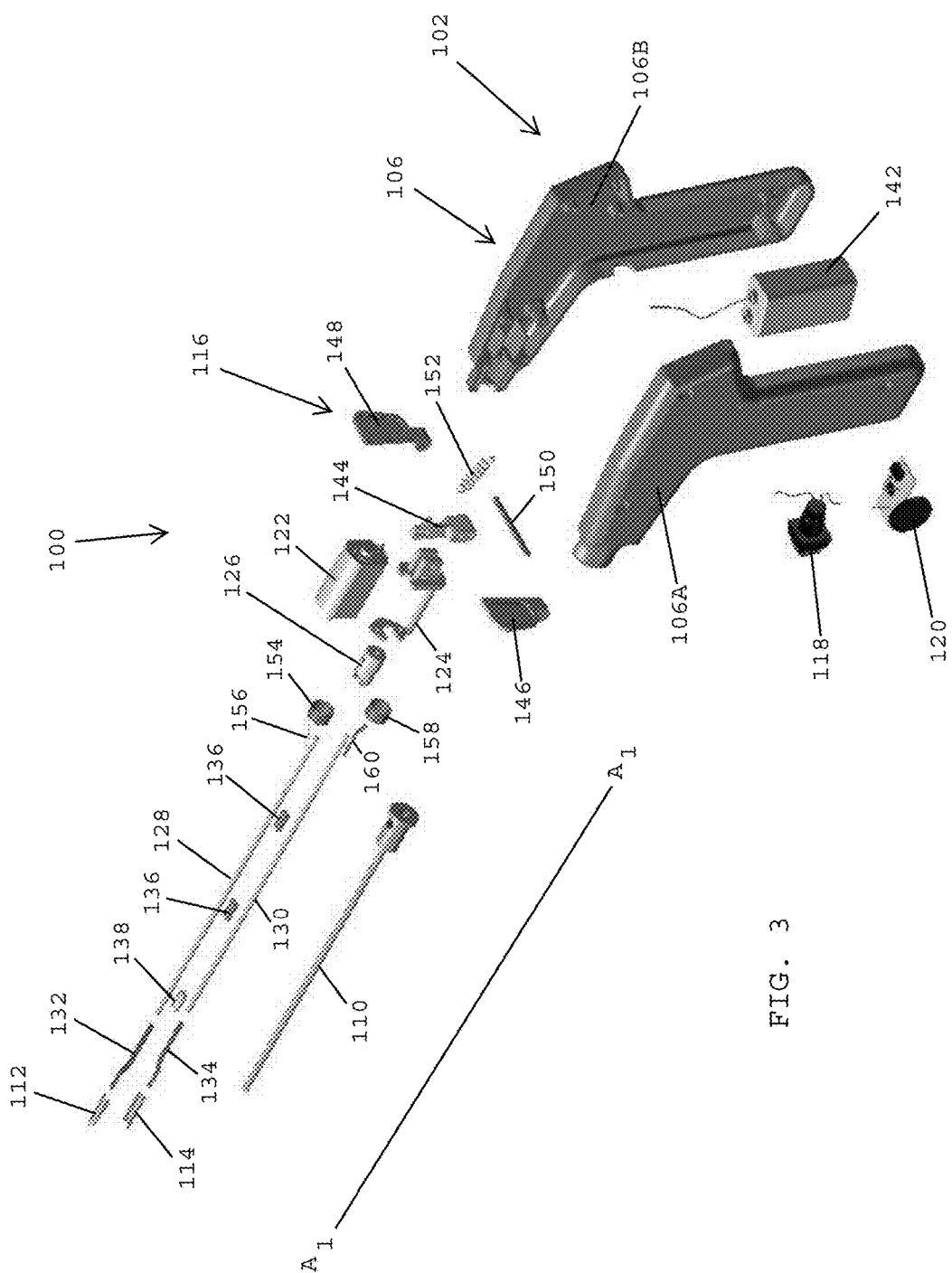
FIG. 3 shows an exploded view of the bipolar medical device for extracting tissue shown in FIGS. 1A-B and 2.
Figure 5A:
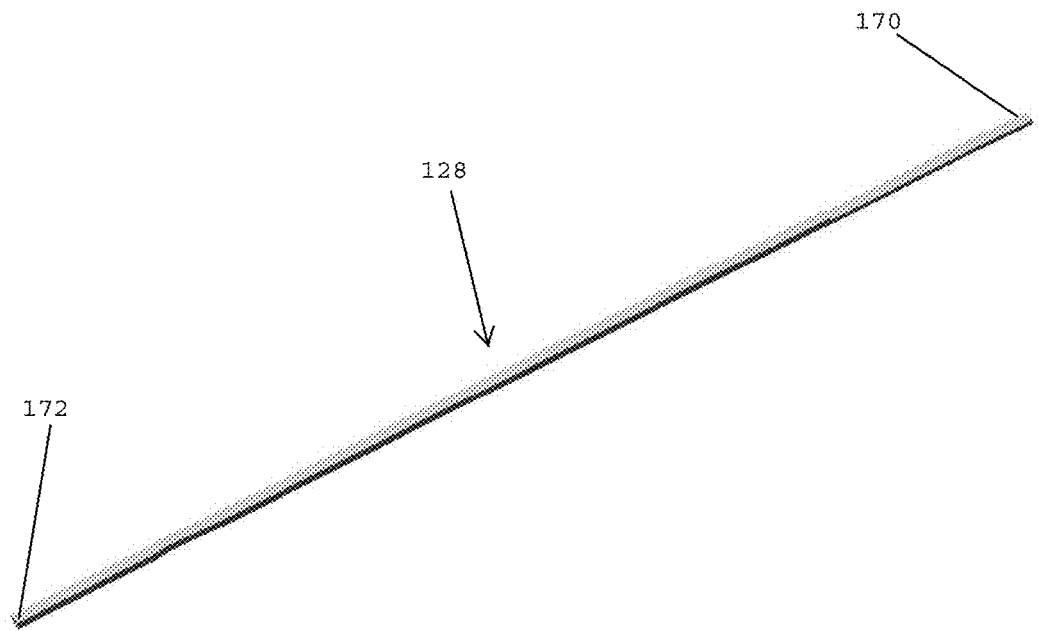
FIG. 5A shows a perspective view of a tong extension of the tissue extraction assembly of FIGS. 4A and 4B.
Figure 5B:
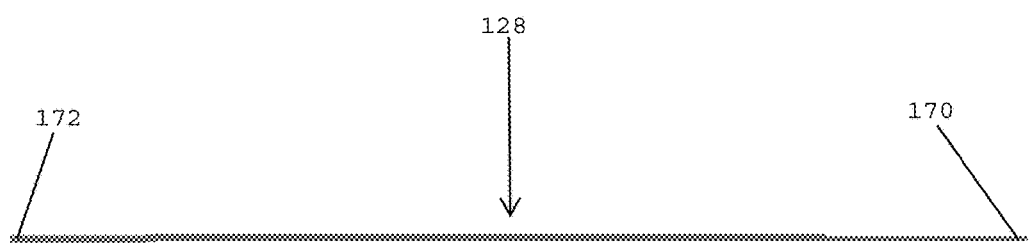
FIG. 5B shows a front elevational view of the tong extension shown in FIG. 5A.
Figure 6A:
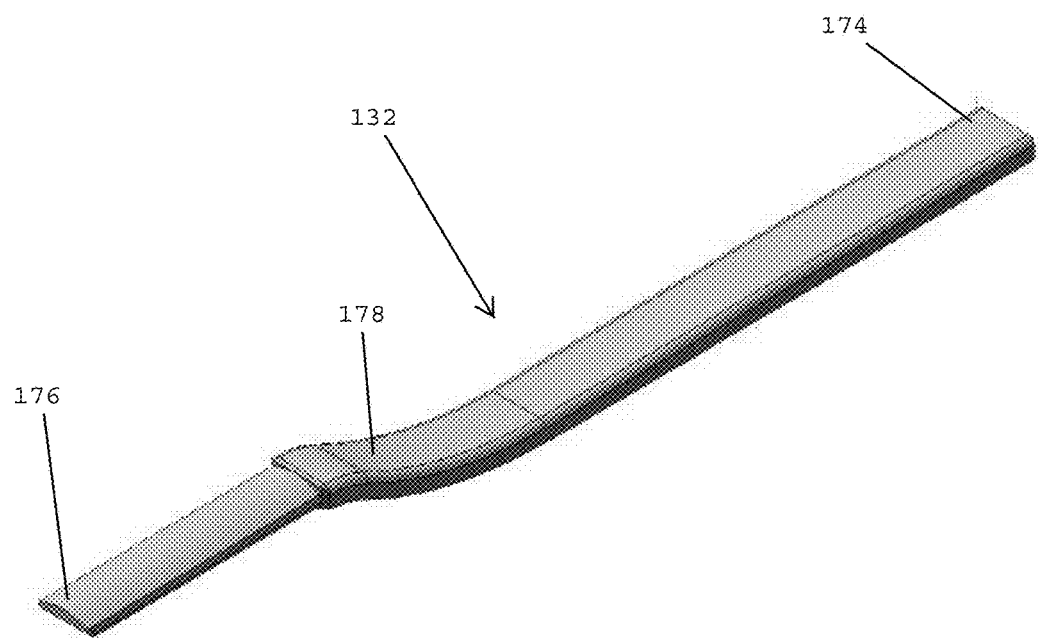
FIG. 6A shows a perspective view of a tong of the tissue extraction assembly of FIGS. 4A and 4B.
Figure 6B:
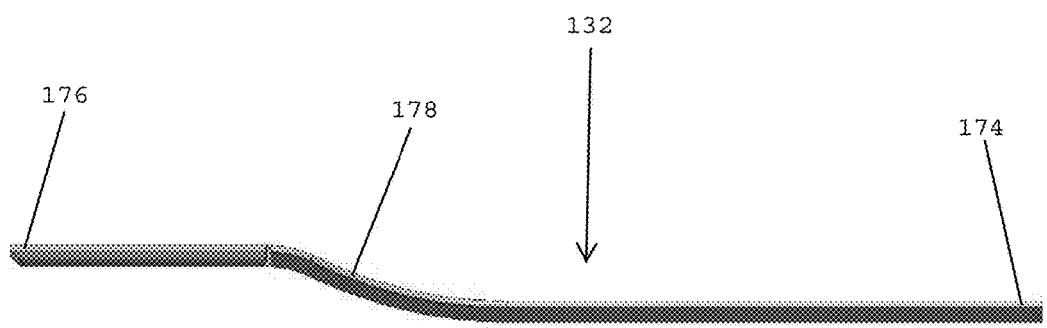
FIG. 6B shows a front elevational view of the tong shown in FIG. 6A.

Referring to FIGS. 2 and 3, in one embodiment, the bipolar medical device 100 preferably includes a lever assembly 116 that is coupled with the first and second cutting elements 112, 114 for selectively advancing the cutting elements along the longitudinal axis $A_1$ toward the distal end 104 of the device 100. The lever assembly 116 may be mounted on the housing 106. The bipolar medical device 100 for extracting tissue also desirably includes a motor actuator 118 that may be engaged for activating a motor (FIG. 2) for rotating the first and second cutting elements 112, 114 about the longitudinal axis $A_1$. In one embodiment, the bipolar medical device 100 preferably includes a motor speed adjustment 120 that may be engaged by surgical personnel for adjusting the speed of rotation of the motor, which, in turn, controls the speed of rotation of the first and second cutting elements 112, 114.

Referring to FIGS. 2 and 3, in one embodiment, the bipolar medical device 100 for extracting tissue preferably includes a motor 122 that is disposed within a motor holder 124. The motor holder 124 is preferably disposed within the device housing 106 and is adapted to slide distally and proximally within the housing 106, along the longitudinal axis $A_1$. In one embodiment, the motor 122 is coupled with the split tube including the first and second cutting elements 112, 114 so that activation of the motor will result in rotation of the first and second cutting elements about the longitudinal axis $A_1$. FIG. 2 shows the housing 106 with a left housing part removed for revealing the components located within the housing. FIG. 3 shows an exploded view including the left housing part 106A and a right housing part 106B that may be assembled together for forming the housing 106.

Referring to FIGS. 2 and 3, the bipolar medical device 100 for extracting tissue desirably includes a motor coupler 126 that is coupled with a drive shaft (FIG. 19A) of the motor 122. Referring to FIGS. 2 and 3, in one embodiment, a distal end of the motor coupler 126 is connected with the respective proximal ends of a first tong extension 128 and a second tong extension 130. The distal ends of the first and second tong extensions 128, 130 are connected with first and second tongs 132, 134, respectively. In turn, the distal end of the first tong 132 is connected with the first cutting element 112 and the distal end of the second tong 134 is connected with the second cutting tube 114.

Referring to FIG. 3, in one embodiment, the bipolar medical device 100 preferably includes one or more tong extension spacers 136 that are disposed between the first and second tong extensions 128, 130. The tong extension spacers 136 desirably keep the first and second tong extensions 128, 130 spaced apart and insulated from one another. The tong extension spacers 136 also desirably keep the tong extensions properly aligned relative to one another, keep the tong extensions together, limit torsional twist during rotation, and keep the tongs from bowing during movement of the first and second cutting elements 112, 114 along the longitudinal axis $A_1$ of the device. The bipolar medical device 100 also desirably includes a tong spacer 138 located distally from the tong extension spacers 136. The tong spacer 138 spaces the tongs 132, 134 away from one another and performs substantially the same functions as described above for the tong extension spacers 136.

Referring to FIGS. 2 and 3, the bipolar medical device 100 also desirably includes the elongated outer tube 110 adapted to project distally from the housing 106. The outer tube 110 has an elongated conduit extending from a proximal end to a distal end thereof. The first and second tong extensions 128, 130 desirably pass through the elongated conduit of the outer tube 110 so that the first and second tongs 132, 134 may project from an opening at the distal end of the outer tube 110.

In one embodiment, the bipolar medical device 100 desirably includes a power source 142 that provides power to the motor 122. In one embodiment, the power source 142 is a battery such as a 9-Volt battery or a lithium battery.

In one embodiment, the bipolar medical device 100 desirably includes an actuation lever 144 disposed within the housing 106. An upper end of the actuation lever 144 is preferably coupled with a proximal end of the motor holder 124. The actuation lever 144 is desirably coupled with the lever assembly 116 including a first thumb lever 146 and a second thumb lever 148. An actuation rod 150 is adapted to extend through a transverse opening at the lower end of the actuation lever 144. The outer ends of the actuation rod 150 are preferably inserted into openings at the lower ends of the first and second thumb levers 146, 148. Surgical personnel may press the first thumb lever 146 and/or the second thumb lever 148 toward the distal end 104 of the device 100 for pivoting the upper end of the actuation lever 144 toward the distal end of the device. As the actuation lever 144 pivots toward the distal end of the device, the actuation lever 144 advances the motor holder 124 and the motor 122 mounted therein in a distal direction, which, in turn, advance the first and second cutting elements 112, 114 toward the distal end of the outer tube 110.

The bipolar medical device 100 also preferably includes a spring 152 having a distal end connected with the actuation lever 144 and a proximal end connected with the housing 106. When the first and/or second thumb levers 146, 148 are pressed toward the distal end of the device 100, the spring 152 is stretched for storing energy therein. When the first and/or second thumb levers 146, 148 are released, the spring 152 pulls the actuation lever 144, the motor holder 124, the motor 122, and the first and second cutting elements 112, 114 toward the proximal end 102 of the device 100.

In one embodiment, the bipolar medical device 100 also desirably includes the motor actuator switch 118 that is coupled with the power source 142. When an operator engages (e.g., depresses) the motor actuator switch 118, the motor 122 is activated for rotating the first and second cutting elements 112, 114 about the longitudinal axis $A_1$. The bipolar medical device 100 preferably includes the motor speed adjuster 120 for enabling an operator to adjust the speed (i.e., rotations per minute or RPM) of the motor 122 and the first and second cutting elements 112, 114.

In one embodiment, the bipolar medical device 100 desirably includes a first bushing 154 electrically coupled with the first tong extension 128 via a first connector 156, and a second bushing 158 electrically coupled with the second tong extension 130 via a second connector 160. As will be described in more detail herein, the first and second bushings 154, 158 are preferably coupled with an electrosurgical generator for electrically energizing the respective first and second cutting tubes 112, 114 with different polarities.

Referring to FIGS. 4A-4B and 5A-5B, in one embodiment, the bipolar medical device 100 preferably includes the first tong extension 128 having a proximal end 170 and a distal end 172. The proximal end 170 is preferably connected with the motor coupler 126, and the distal end 172 is preferably connected with the first tong 132. The first tong extension 128 is preferably made of a conductive material such as stainless steel. In one embodiment, the first tong extension 128 has a length of approximately 6.5-7.0 inches. The second tong extension 130 preferably has the same features as described herein for the first tong extension 128.

Referring to FIGS. 4A-4B and 6A-6B, in one embodiment, the first tong 132 has a proximal end 174 connected with the distal end 172 of the first tong extension 128 and a distal end 176 connected with the first cutting element 112. The first tong 132 desirably includes a curved section 178 that is provided so that the first and second tongs 132, 134 are normally biased away from one another. The second tong 134 preferably has the same features as described herein for the first tong 132. The first and second tongs 132, 134 preferably have a spring temper with a slight curvature that generates a bias away from one another, which facilitates opening the tongs 132, 134 to release tissue therebetween.

Referring to FIGS. 4A-4B and 7A-7D, the first cutting element 112 of the split cutting tube preferably includes a semi-tubular body 180 having a convex top surface 182 and a concave bottom surface 184. The semi-tubular body 180 has a proximal end 186 connected with the distal end 176 of the first tong 132. The semi-tubular body 180 also desirably includes a distal end 188 having a distal cutting surface 190, a first angled cutting surface 192 and a second angled cutting surface 194. The semi-tubular body 180 also desirably includes a cutting tooth 196 projecting from the concave bottom surface 184. In one embodiment, the cutting tooth 196 is formed by punching out a section of the semi-tubular body 180 and bending the punched-out section downwardly so that it projects radially inward from the concave bottom surface 184.

Figure 7A:
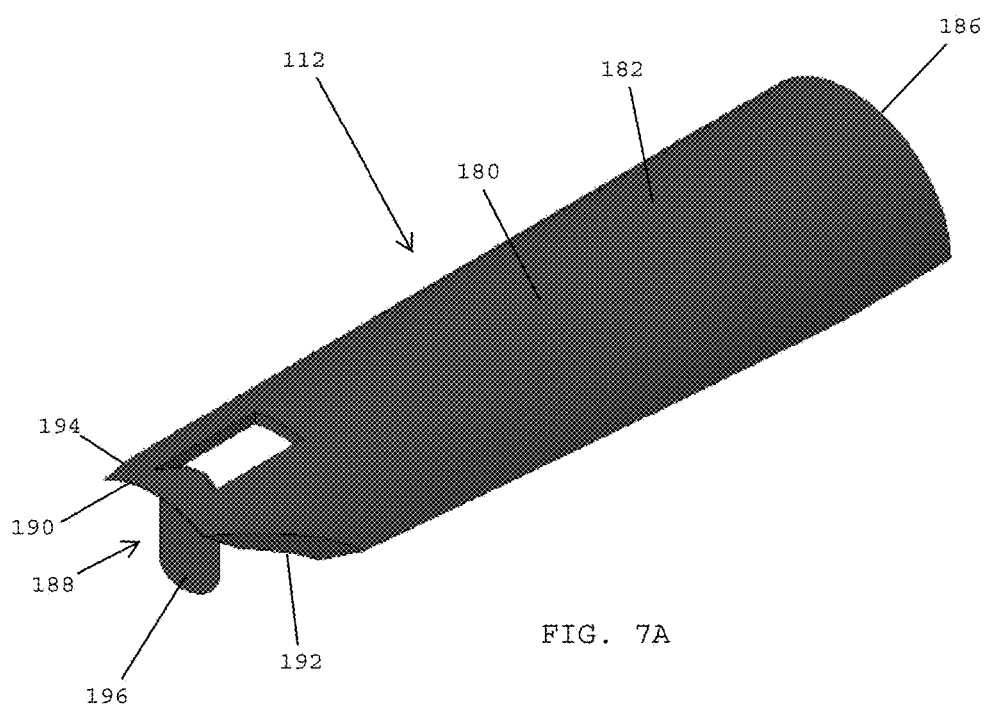
FIGS. 7A-7D show a first cutting element of a split cutting tube of the tissue extraction assembly of FIGS. 4A and 4B.
Figure 7B:
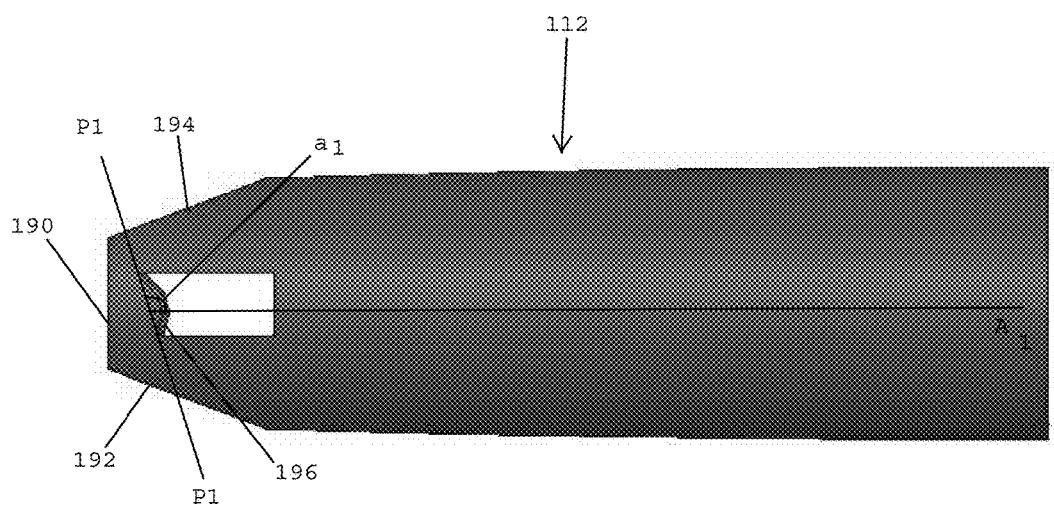
Figure 7C:
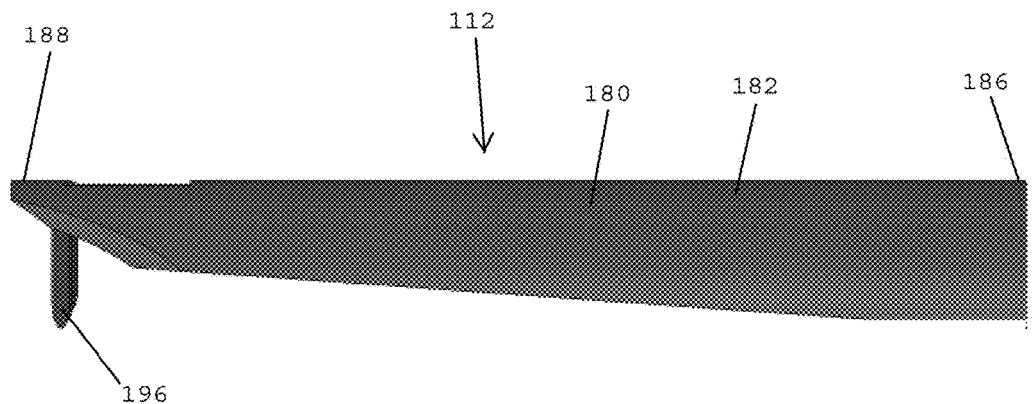
Figure 7D:
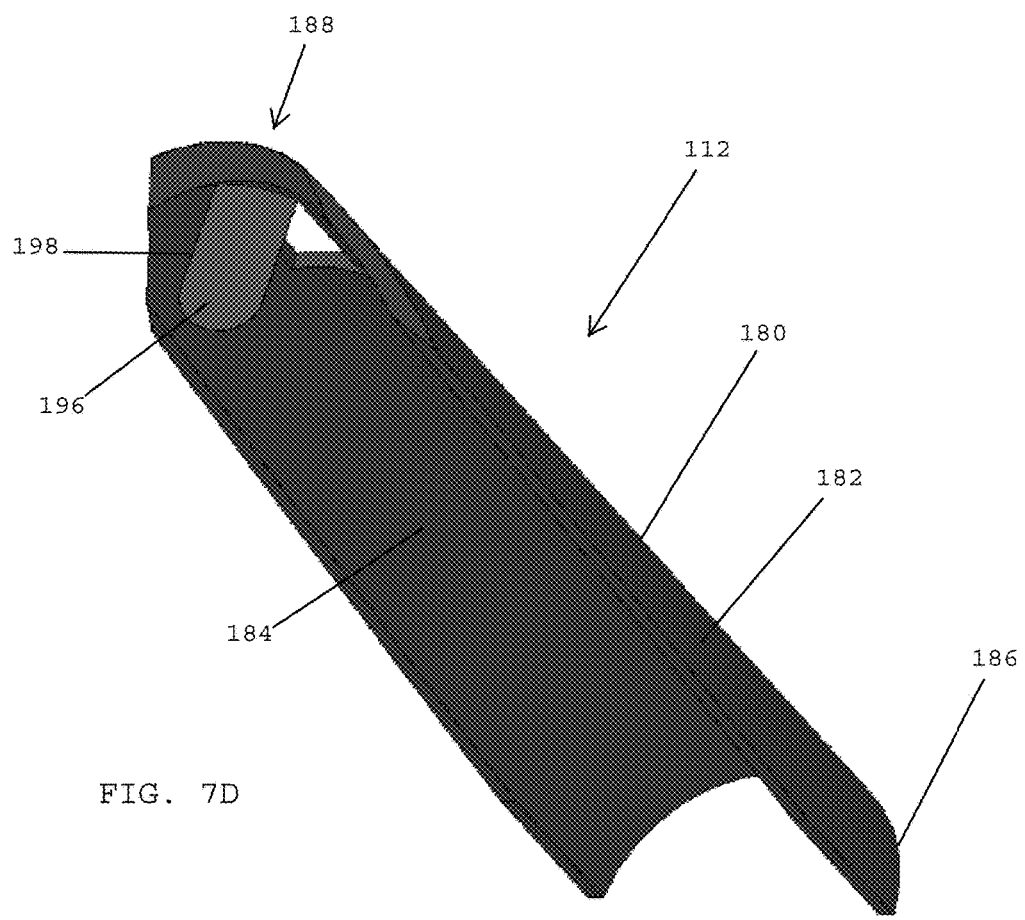
Figure 8A:
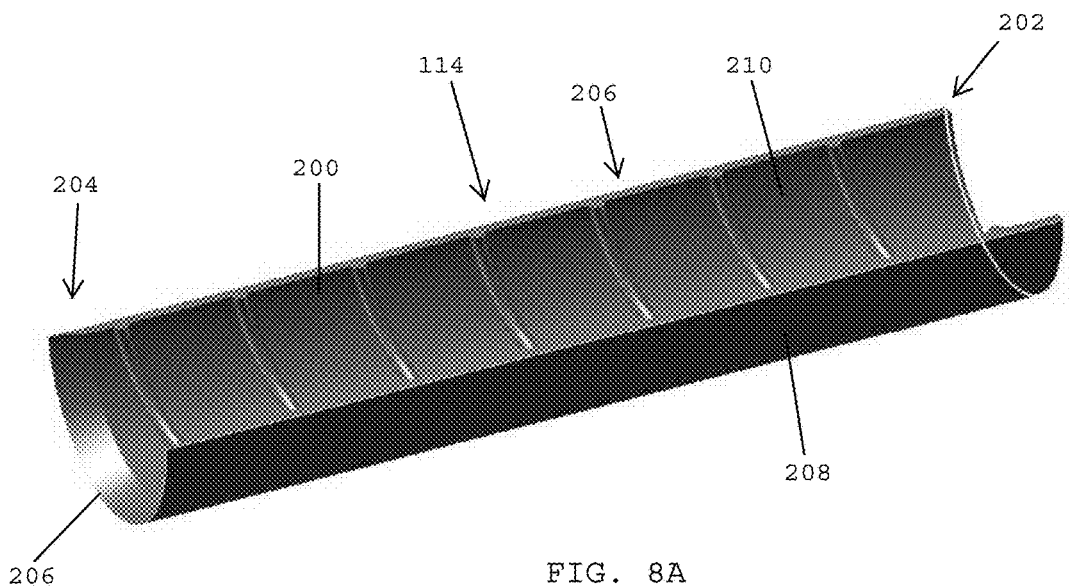
FIGS. 8A-8C show a second cutting element of a split cutting tube of the tissue extraction assembly of FIGS. 4A and 4B.
Figure 8B:
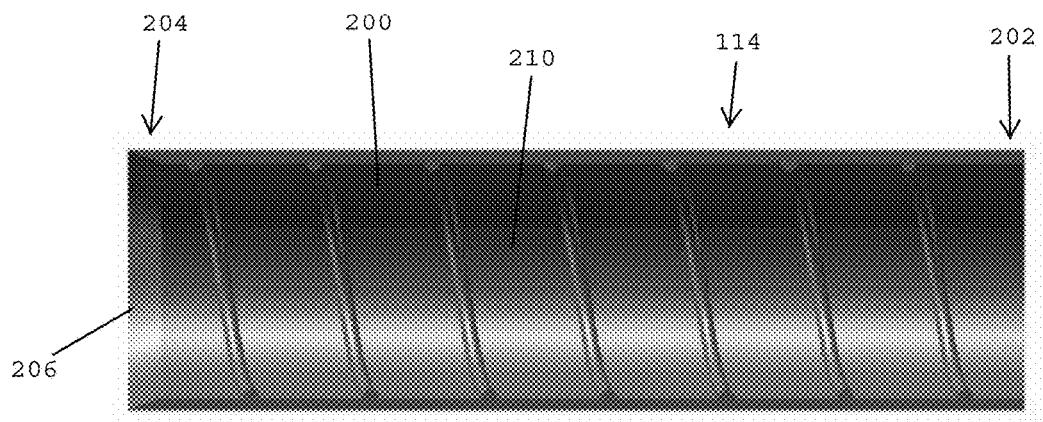
Figure 8C:
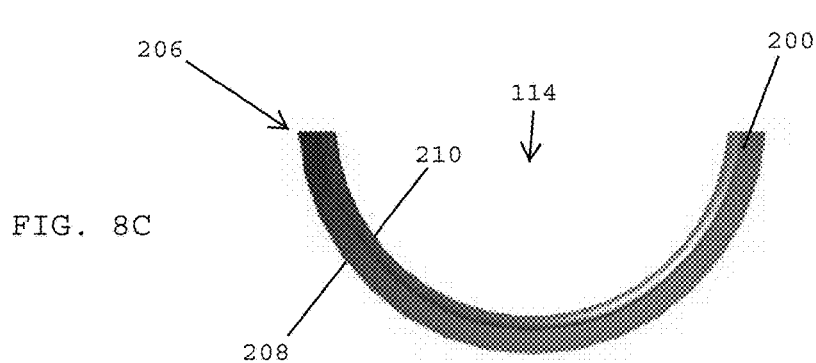
Figures 9A, 9B:
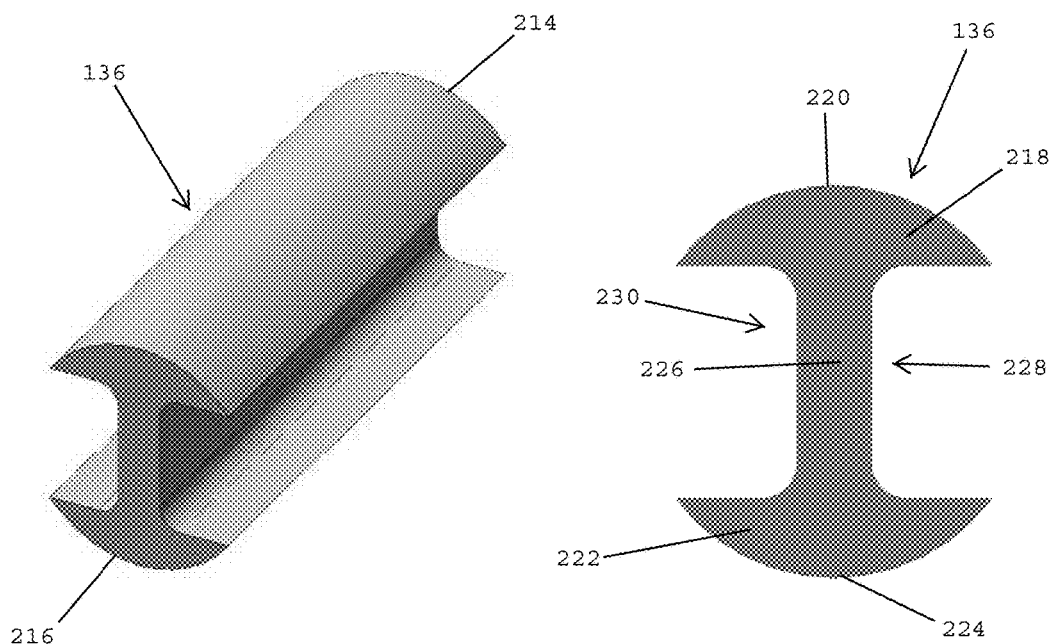
FIGS. 9A and 9B show a tong extension spacer of the tissue extraction assembly of FIGS. 4A and 4B, in accordance with one embodiment of the present invention.
Figures 10A, 10B:
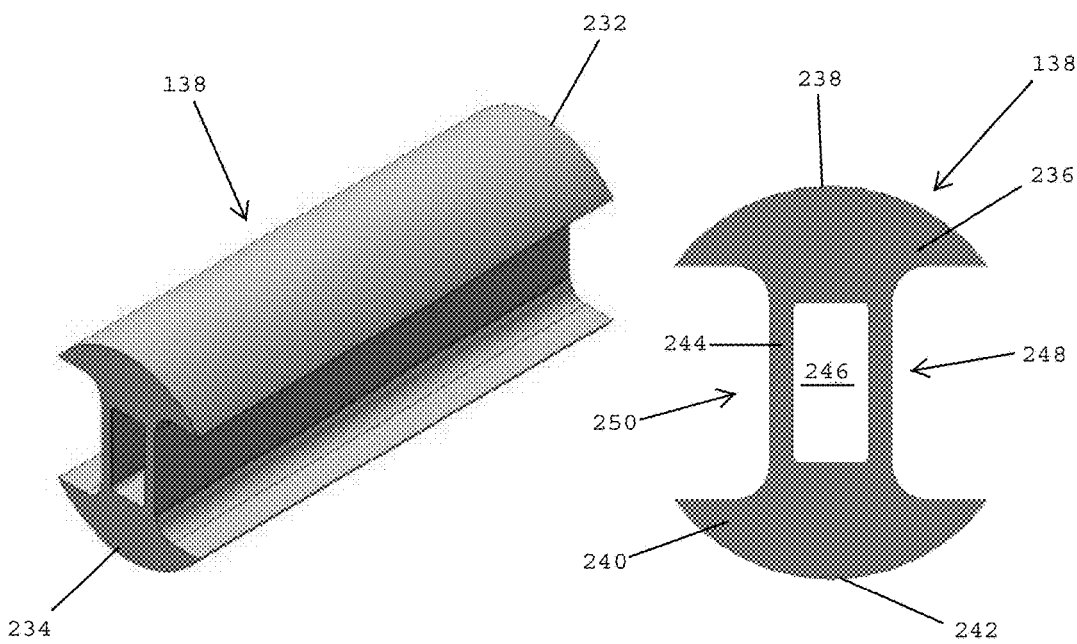
FIGS. 10A and 10B show a tong spacer of the tissue extraction assembly of FIGS. 4A and 4B, in accordance with one embodiment of the present invention.

Referring to FIG. 7B, in one embodiment, the cutting tooth 196 extends within a plane $P_1$ that forms an angle $a_1$ of greater than 90° with the longitudinal axis $A_1$. Although the present invention is not limited by any particular theory of operation, it is believed that angling the cutting tooth 196 so that it lies within a plane that forms an obtuse angle with the longitudinal axis $A_1$ creates a helical angle for the cutting tooth 196 that enables the first cutting element 112 to more efficiently cut through tissue. Referring to FIG. 7D, in one embodiment, the leading edge 198 of the angled cutting tooth 196 is sharpened for enhancing cutting through tissue as the first cutting element 112 rotates about the longitudinal axis. In one embodiment, the first cutting element 112 is preferably made of a conductive material such as stainless steel so that electrical signals may pass through the semi-tubular body 180.

FIGS. 4A-4B and 8A-8C show the second cutting element 114 that opposes the first cutting element 112. The second cutting element 114 preferably includes a semi-tubular body 200 having a proximal end 202 adapted to be connected with the distal end of the second tong 134 and a distal end 204 having a distal cutting edge 206. The semi-tubular body 200 of the second cutting element 114 preferably includes a convex outer surface 208 and a concave inner surface 210.

Referring to FIGS. 4A-4B and 9A-9B, in one embodiment, each tong extension spacer 136 preferably has a proximal end 214 and a distal end 216. The tong extension spacer 136 preferably includes a first section 218 having a convex outer surface 220 and a second section 222 having a convex outer surface 224. The convex outer surfaces 220, 224 preferably enable the tong extension spacer 136 to move axially along the longitudinal axis $A_1$ and to rotate about the longitudinal axis $A_1$ relative to the outer tube 110 (FIG. 2). A connector beam 226 desirably extends between the first section 218 and the second section 222 of the tong extension spacer 136. In one embodiment, the tong extension spacer 136 desirably includes a first elongated groove 228 adjacent a first face of the beam 226 that extends between the first section and second sections 218, 222, and a second elongated groove 230 adjacent a second face of the beam 226 that extends between the first and second sections 218, 222. The first and second elongated grooves 228, 230 are preferably adapted to receive, align and hold therein the first and second tong extensions 128, 130, respectively. The tong extension spacer 136 is preferably made of an insulating material, such as a polymer. In the embodiment shown in FIG. 4A, there are two tong extension spacers 136, however, other embodiments may have fewer or more tong extension spacers 136 and still fall within the scope of the present invention.

Referring to FIGS. 4A-4B and 10A-10B, in one embodiment, the bipolar medical device also desirably includes a tong spacer 138 having a proximal end 232 and a distal end 234. The tong spacer 138 desirably includes a first section 236 having a first convex outer surface 238 and a second section 240 having a second convex outer surface 242. The convex outer surfaces 238, 242 preferably enable the tong spacer 138 to move axially and rotate relative to the outer tube 110 (FIG. 2). The tong spacer 138 preferably includes a support beam 244 that interconnects the first and second sections 236, 240 and extends along the length of the tong spacer 138. In one embodiment, an elongated conduit 246 extends through the support beam 244, which may be used for enabling tools such as tissue grasping tools to be passed therethrough for grasping cut tissue pieces and removing the cut pieces through the elongated conduit 246. The tong spacer 138 preferably includes a first elongated groove 248 extending between the first section 236 and the second section 240 and along the length of the tong spacer, and a second elongated groove 250 extending between the first section 236 and the second section 240 and along the length of the tong spacer. In one embodiment, the first and second elongated grooves 248, 250 are adapted to seat distal ends of the first and second tong extensions 128, 130, respectively. In one embodiment, the first and second grooves 248, 250 are adapted to seat the first and second tongs 132, 134, respectively. The tong spacer 138 is preferably made of an insulating material that prevents electrical arcing between the first and second tong extensions 128, 130 and/or the first and second tongs 132, 134.

Figure 11A:
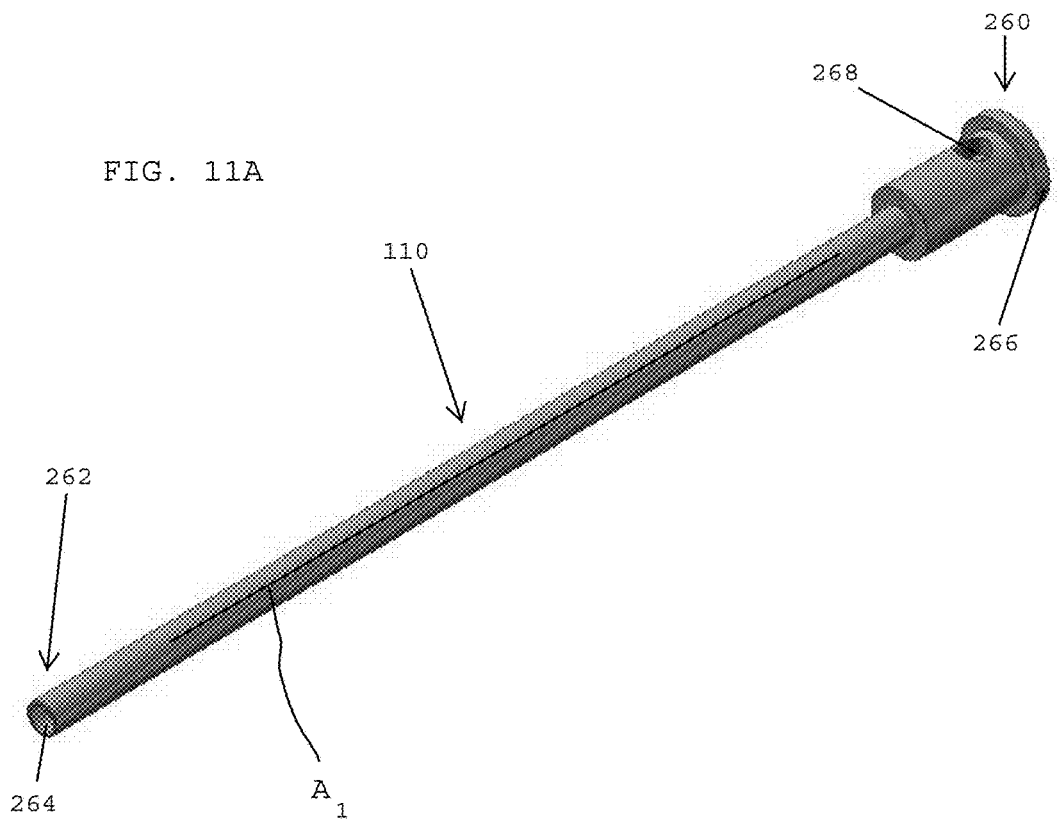
FIGS. 11A-11C show an outer tube of a bipolar medical device for extracting tissue, in accordance with one embodiment of the present invention.
Figure 11B:
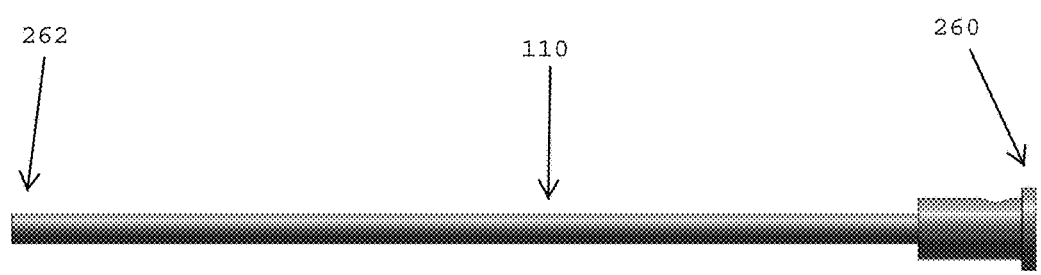

Referring to FIGS. 11A-11B, in one embodiment, the bipolar medical device for extracting tissue preferably includes the outer tube 110 that projects from the distal end of the device housing 106 (FIG. 2). In one embodiment, the outer tube 110 is preferably made of a conductive material such as stainless steel and preferably includes a proximal end 260, a distal end 262 and an elongated conduit or opening 264 extending along the length of the outer tube between the proximal and distal ends 260, 262. In one embodiment, the outer tube 110 has a diameter of about 5 mm, which is selected based upon patient comfort, ability to remove a sufficient amount of tissue and other mechanical considerations. The outer tube 110 preferably includes an annular flange 266 located at the proximal end 260. Referring to FIGS. 2 and 11A, in one embodiment, the annular flange 266 is preferably seated within a groove formed in the device housing 106 for mounting the outer tube 110 to the distal end of the device housing, which desirably keeps the outer tube axially stationary.

Referring to FIG. 11A, in one embodiment, the outer tube is adapted to rotate with the first and second tong extensions 128, 130 (FIG. 4A) about the longitudinal axis $A_1$ using the annular flange 266 and the groove formed in the device housing 106. In another embodiment, the proximal end 260 of the outer tube 110 may include one or more fastener openings 268 that receive fasteners coupled with the housing 106 that keep the outer tube rotationally stationary.

Figure 11C:
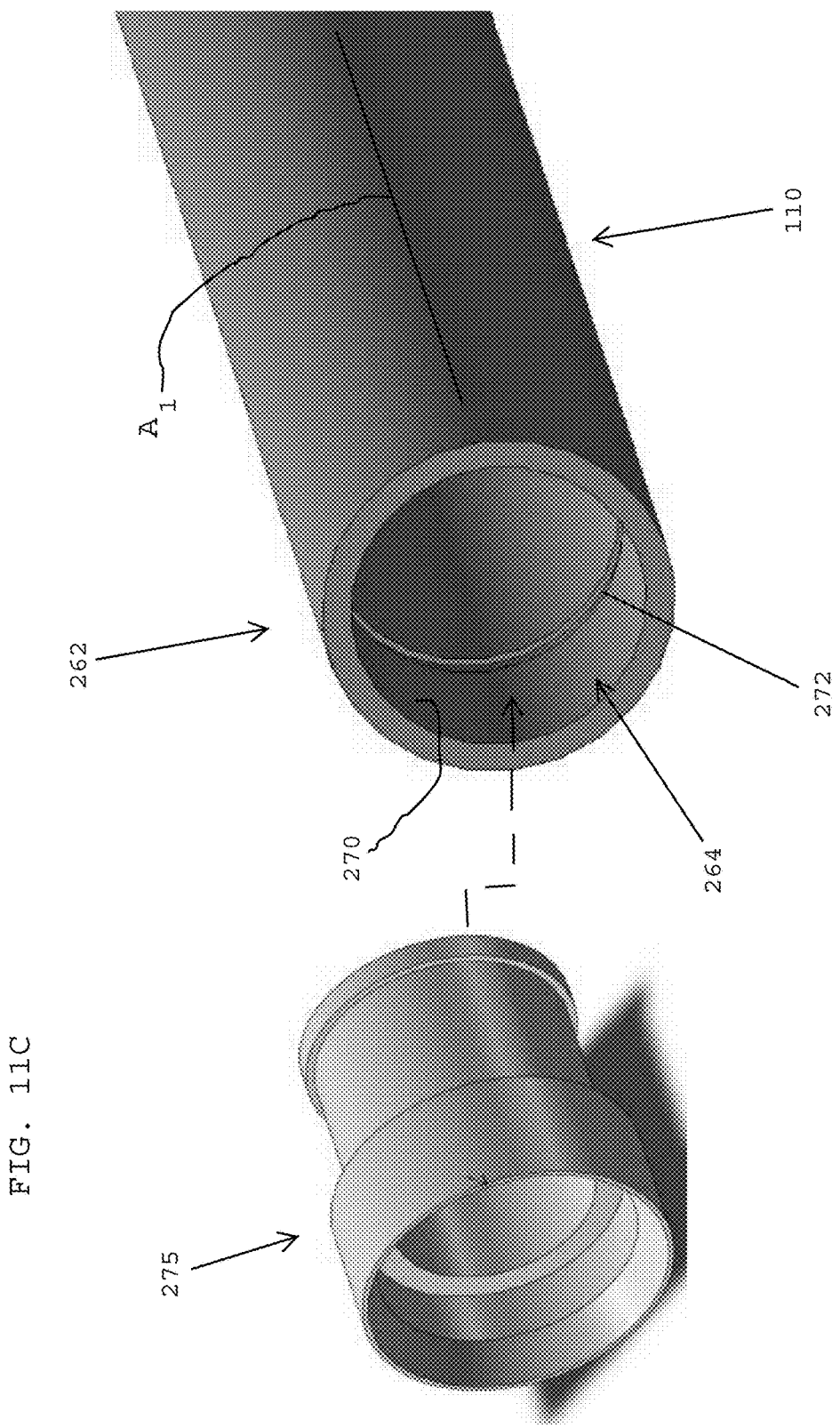

Referring to FIG. 11C, in one embodiment, the inner surface 270 of the outer tube 110, adjacent the distal end 262 thereof, has an annular groove 272 formed therein. The annular groove 272 may be used for coupling an outer tube extension 275 to the distal end 262 of the outer tube 110. In one embodiment, the outer tube extension 275 may be adapted to rotate freely relative to the distal end 262 of the outer tube 110. In one embodiment, the outer tube extension 275 is made of a non-conductive material and serves as an insulator. In one embodiment, the outer tube extension 275 may rotate simultaneously with the outer tube 110 about the longitudinal axis $A_1$. The outer tube extension 275 is preferably made of an insulating material, such as a polymer material, that keeps the first and second cutting elements 112, 114, and the first and second tongs 132, 134 insulated from one another and from the metal outer tube 110. In one embodiment, the outer tube extension 275 may be a machined part that is secured to a distal end of the outer tube 110 such as by using a chamfered fit. In this latter embodiment, insulation may be wrapped around the first and second tongs 143, 134 and proximal portions of the first and second cutting elements 112, 114 for insulating the first and second cutting elements from one another and from the conductive outer tube. In one embodiment, the outer tube extension 275 may be made of a lubricious polymeric material.

Figure 12:
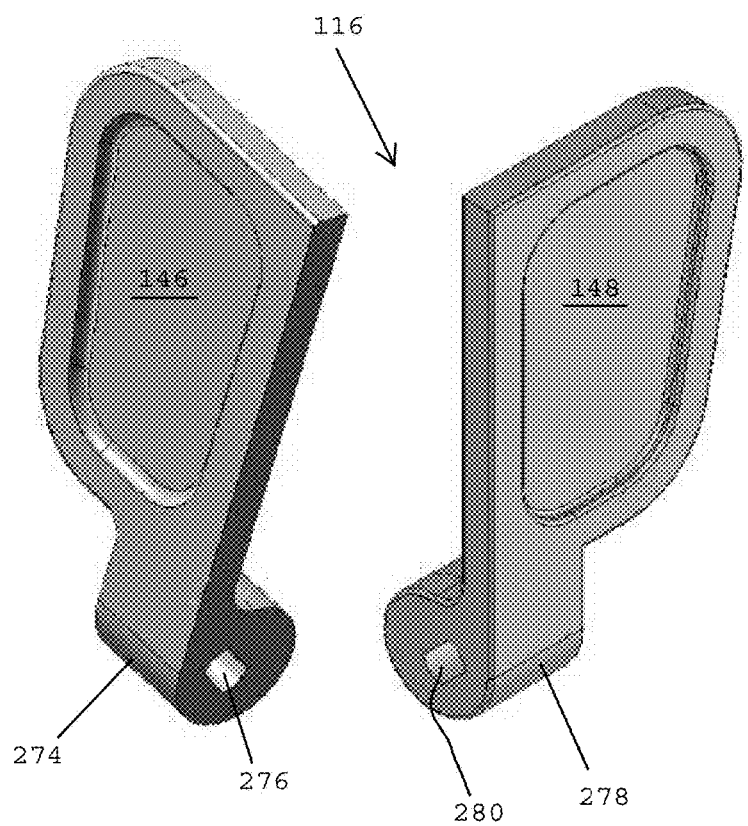
FIG. 12 shows a lever assembly for a bipolar medical device for extracting tissue including first and second thumb levers, in accordance with one embodiment of the present invention.

Referring to FIGS. 1A and 12, in one embodiment, the bipolar medical device 100 preferably includes the lever assembly 116 having a first thumb lever 146 and a second thumb lever 148. The first thumb lever 146 has a lower end 274 with a first blind opening 276 extending transversely therethrough. The second thumb lever 148 also has a lower end 278 with a second blind opening 280 extending transversely therethrough.

Figure 13:
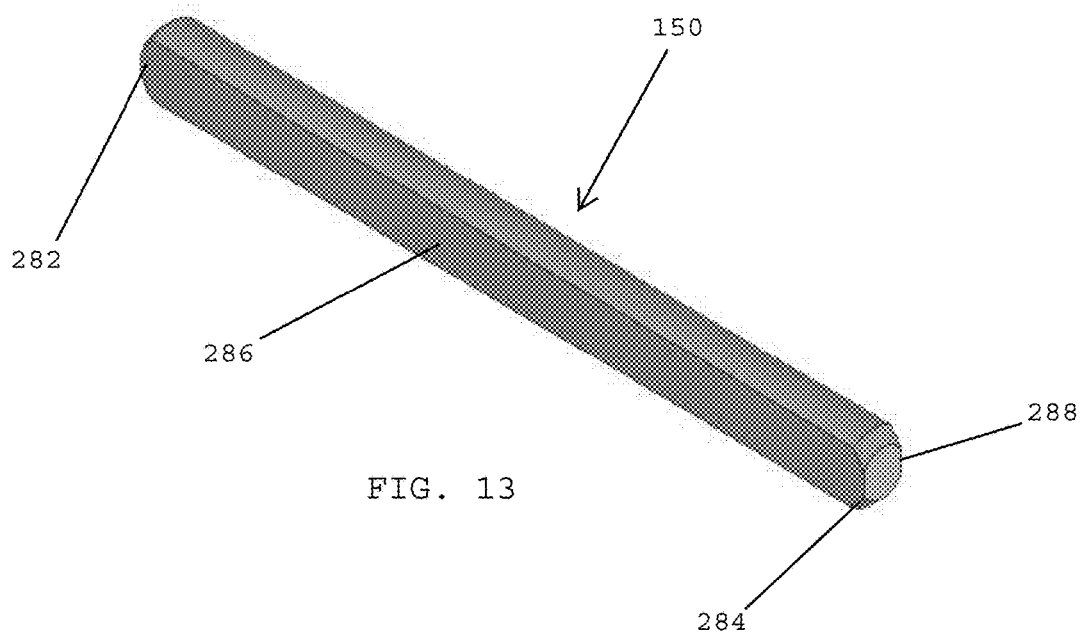
FIG. 13 shows an actuation rod assembled with the first and second thumb levers of FIG. 12, in accordance with one embodiment of the present invention.

Referring to FIGS. 12 and 13, the first and second thumb levers 146, 148 are adapted for being assembled with the actuation rod 150. The actuation rod 150 desirably has a first end 282 adapted for being inserted into the first blind opening 276 of the first thumb lever 146, and a second end 284 adapted for being inserted into the second blind opening 280 of the second thumb lever 148. The actuation rod preferably includes a first flat surface 286 and a second flat surface 288 that desirably extend on opposite sides of the actuation rod between the first end 282 and the second end 284 thereof. The flat surfaces 286, 288 of the actuation rod 150 are desirably received in the respective first and second blind openings 276, 280 and abut against flat surfaces of the respective first and second blind openings 276, 280 so that the thumb levers 146, 148 and the actuation rod 150 pivot simultaneously with one another.

Referring to FIGS. 14A and 14B, in one embodiment, the bipolar medical device 100 desirably includes the actuation lever 144 (FIGS. 2 and 3) having an upper end 290 and a lower end 292. The upper end 290 of the actuation lever 144 preferably includes a motor holder connection opening 294 defining an elongated slot. The motor holder connection opening 294 is adapted for being aligned with a proximally located flange on the motor holder 124 (FIGS. 2 and 3). A pin or fastener (not shown) may be passed through the motor holder connection opening 294 for coupling the upper end 290 of the actuation lever 144 with proximally extending flanges on the motor holder 124.

The lower end 292 of the actuation lever 144 preferably includes an actuation rod opening 296 that extends transversely through the actuation lever 144. The actuation rod opening 296 has opposing flat surfaces 298, 300 that are adapted to engage the flat elongated surfaces 286, 288 of the actuation rod 150 (FIG. 13).

In one embodiment, the actuation rod 150 passes through the actuation rod opening 296 with the first end 282 of the actuation rod connected with the first thumb lever 146 (FIG. 12) and the second end 284 of the actuation rod connected with the second thumb lever 148 (FIG. 12). In one embodiment, the actuation lever 144 also desirably includes a spring retaining flange 302 having a spring retaining opening 304 extending therethrough.

Referring to FIGS. 14A-14B and 15, in one embodiment, the spring 152 has a proximal end 306 adapted to be connected with the housing 106 (FIG. 2) and a distal end 308 adapted to be coupled with the spring retaining flange 302 of the actuation lever 144. In one embodiment, a loop 310 at the distal end 308 of the spring 152 may be passed through the opening 304 of the spring retaining flange 302 for coupling the spring 152 with the actuation lever 144.

Figure 16:
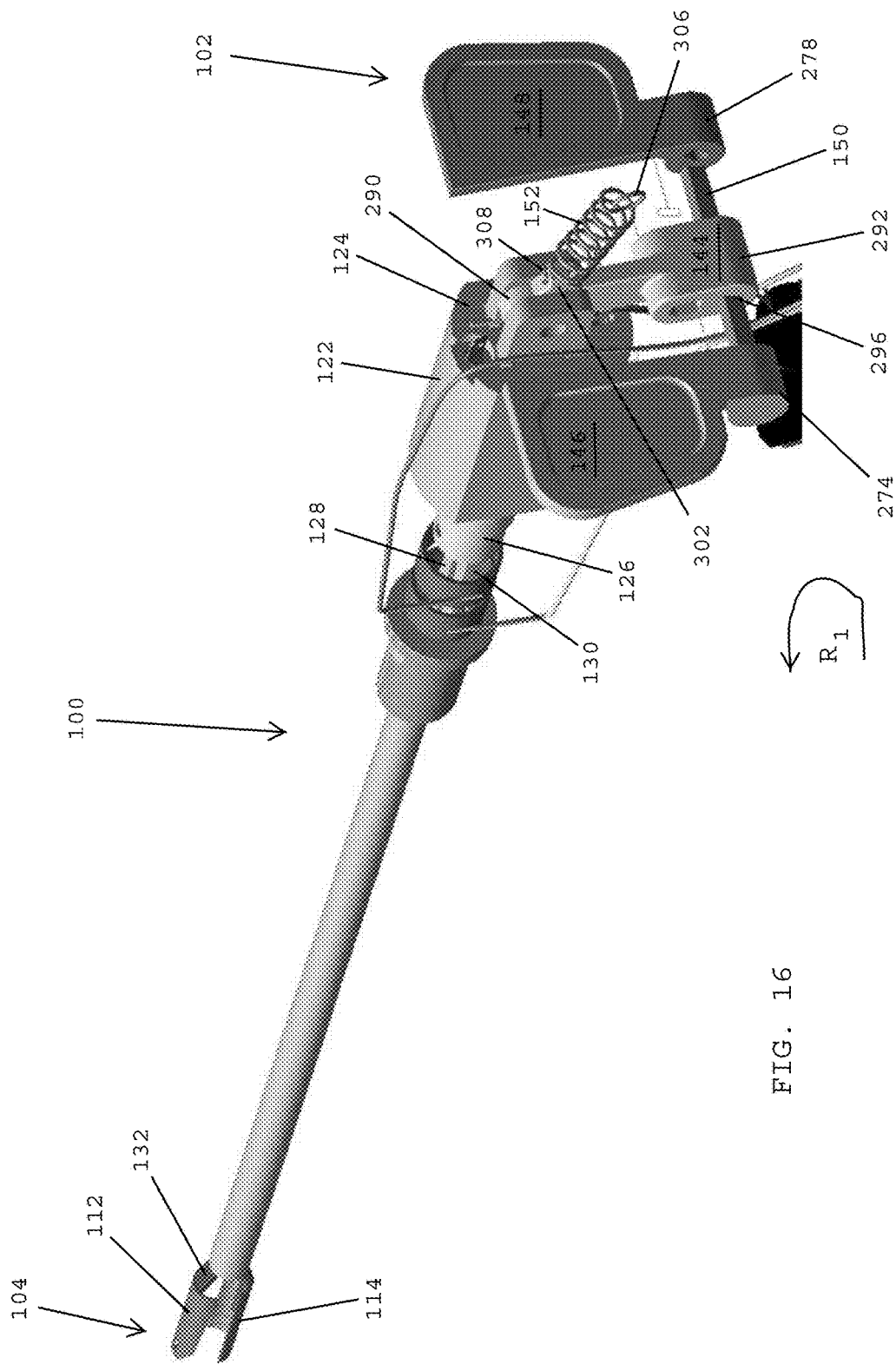
FIG. 16 shows a rear perspective view of a lever assembly including the first and second thumb levers of FIG. 12 and the actuation lever of FIGS. 14A and 14B.

Referring to FIGS. 14A-14B and 16, in one embodiment, the actuation rod 150 is desirably passed through the actuation rod opening 296 at the lower end 292 of the actuation lever 144. A first end of the actuation rod 150 is connected with the first thumb lever 146 and the second end of the actuation rod 150 is connected with the second thumb lever 148. The upper end 290 of the actuation lever 144 is connected with a proximally located connection flange on the motor holder 124. The distal end 308 of the spring 152 is connected with the spring retaining flange 302 adjacent the upper end 290 of the actuation lever 144, and the proximal end 306 of the spring 152 is preferably connected with the housing 106 (FIG. 2).

Referring to FIG. 16, in one embodiment, the first and/or second thumb levers 146, 148 may be pressed toward the distal end 104 of the bipolar medical device 100. As the thumb levers 146, 148 are pressed distally, the linkage between the lower ends 274, 278 of the respective first and second thumb levers 148, 148 rotates the actuation rod 150 in a counterclockwise direction designated $R_1$. As the actuation rod 150 rotates in the counterclockwise direction, the actuation rod 150, in turn, rotates the actuation lever 144 in the counterclockwise direction. The upper end 290 of the actuation lever 144 swings about the lower end 292 thereof for advancing the motor holder 124, the motor 122, the motor coupler 126, the first and second tong extensions 128, 130, the first and second tongs 132, 134, and the first and second cutting elements 112, 114 toward the distal end 104 of the medical device 100. As the motor holder 124 moves distally, the spring 152 is stretched for storing energy therein. When the distally directed force on the first and second thumb levers 146, 148 is removed, the spring 152 pulls the motor holder 124, the motor 122, the motor coupler 126, the tong extensions 128, 130, the tongs 132, 134, and the first and second cutting tubes 112, 114 toward the proximal end 102 of the medical device 100.

Figure 17A:
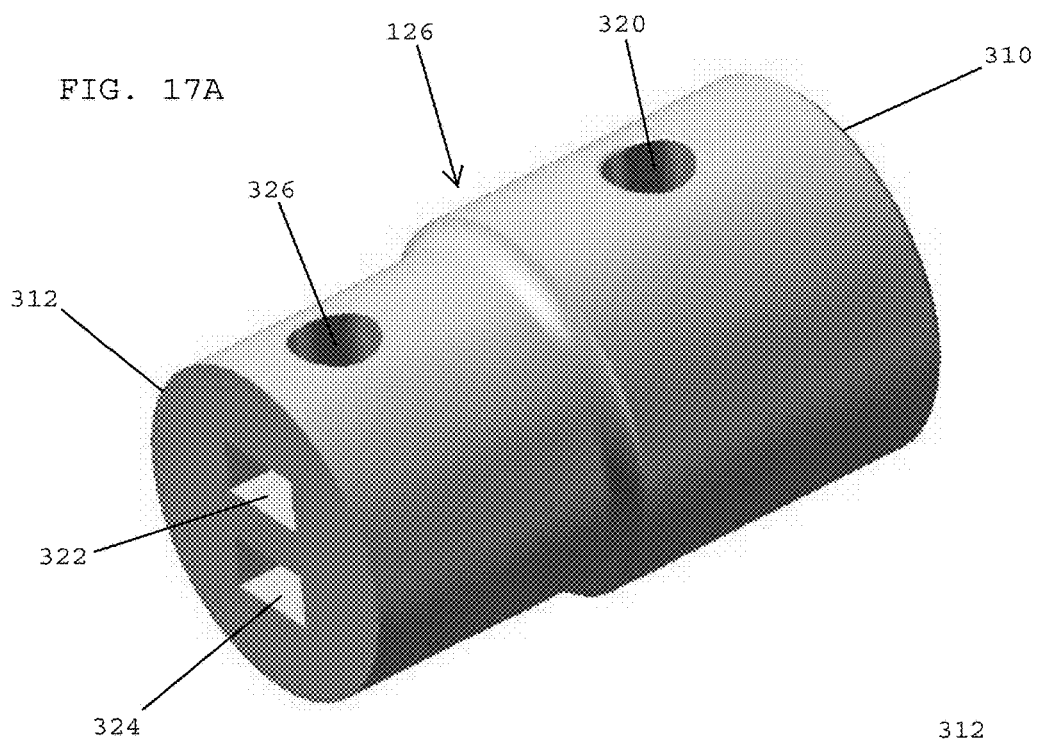
FIGS. 17A and 17B show a motor coupler of a bipolar medical device for extracting tissue, in accordance with one embodiment of the present invention.
Figure 17B:
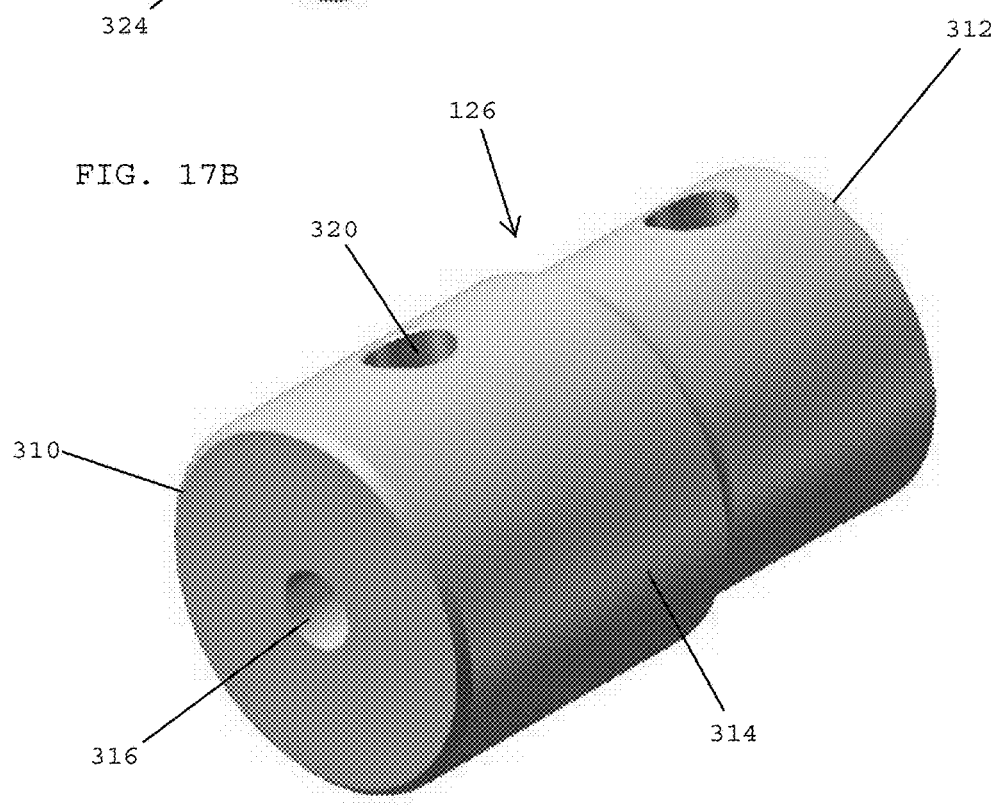

Referring to FIGS. 2 and 17A-17B, in one embodiment, the bipolar medical device 100 desirably includes the motor coupler 126 adapted to couple the motor 122 with the first and second tong extensions 128, 130 (FIG. 2). The motor coupler 126 preferably includes a proximal end 310, a distal end 312 and a tubular body 314 extending between the proximal and distal ends. The proximal end 310 of the motor coupler 126 preferably includes a central opening 316 adapted to receive a drive shaft of the motor 122 (FIG. 2). The motor coupler 126 desirably includes a motor drive shaft fastener opening 320 adapted to receive a fastener for securing the motor coupler 126 to the motor drive shaft so that the motor coupler 126 rotates simultaneously with the motor drive shaft.

The distal end 312 of the motor coupler 126 preferably includes a first opening 322 adapted to receive a proximal end of the first tong extension 128 and a second opening 324 adapted to receive a proximal end of the second tong extension 130 (FIGS. 4A and 4B). The motor coupler 126 also desirably includes a first tong extension fastener opening 326 adapted to receive a fastener that engages the proximal end of the first tong extension 128. The motor coupler 126 also desirably includes a second tong extension fastener opening (not shown) adapted to receive a second fastener that engages the proximal end of the second tong extension 130. When the tong extension fasteners have been inserted into the respective first and second tong extension fastener openings 326, 328, the motor coupler 126 and the tong extensions 128, 130 desirably travel axially together along the longitudinal axis $A_1$ and rotate simultaneously with one another about the longitudinal axis $A_1$ (FIG. 2).

Figure 18:
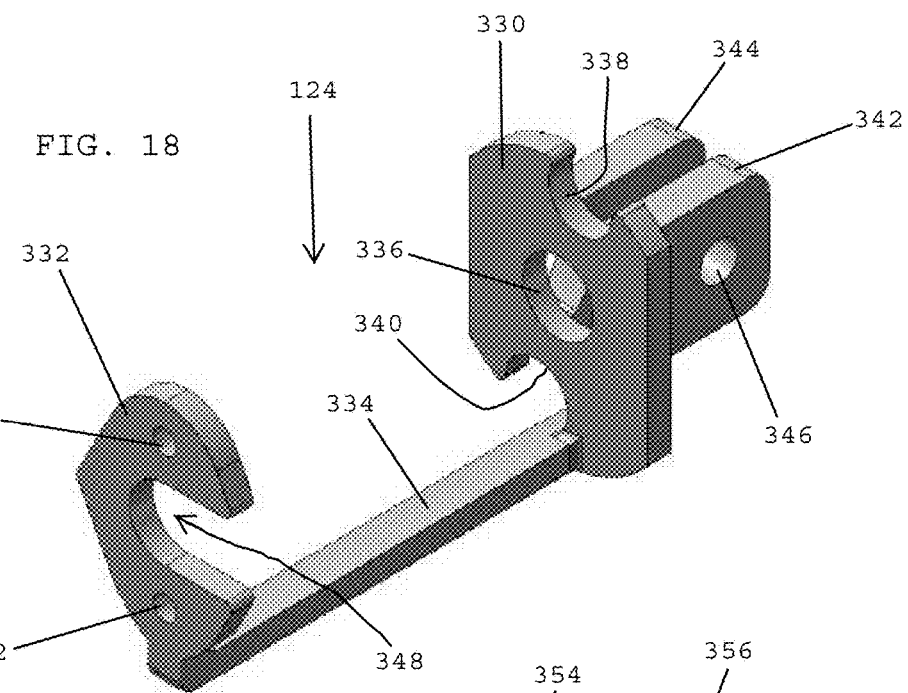
FIG. 18 shows a perspective view of a motor holder of a bipolar medical device for extracting tissue, in accordance with one embodiment of the present invention.

Referring to FIG. 18, in one embodiment, the motor holder 124 (FIG. 2) desirably includes a first plate 330 adjacent a proximal end of the motor holder and a second plate 332 adjacent a distal end of the motor holder. The motor holder 124 also desirably includes a horizontally extending support member 334 that extends from the first plate 330 to the second plate 332. In one embodiment, the first plate 330 includes a central opening 336 adapted to support a central hub on a rear face of the motor 122 (FIG. 2). The first plate 330 includes a first C-shaped opening 338 adjacent an upper end of the first plate 330 and a second C-shaped opening 340 adjacent a lower end of the first plate 330. The motor holder 124 also desirably includes a first proximally extending connection flange 342 and a second proximally extending connection flange 344. The first connection flange 342 preferably has a transverse opening 346 extending therethrough, and the second connection flange 344 has a similar transverse opening (not shown). A fastener such as a pin may be passed through the transverse openings in the first and second proximally extending connection flanges of the motor holder for coupling the actuation lever 144 (FIG. 2) with the motor holder 124.

The motor holder 124 preferably includes the second plate 332 having a C-shaped opening 348 formed therein. The second plate 332 desirably includes motor fastener openings 350, 352 adapted to receive motor fasteners for securing the motor 122 (FIG. 2) to the second plate 332.

Figure 19A:
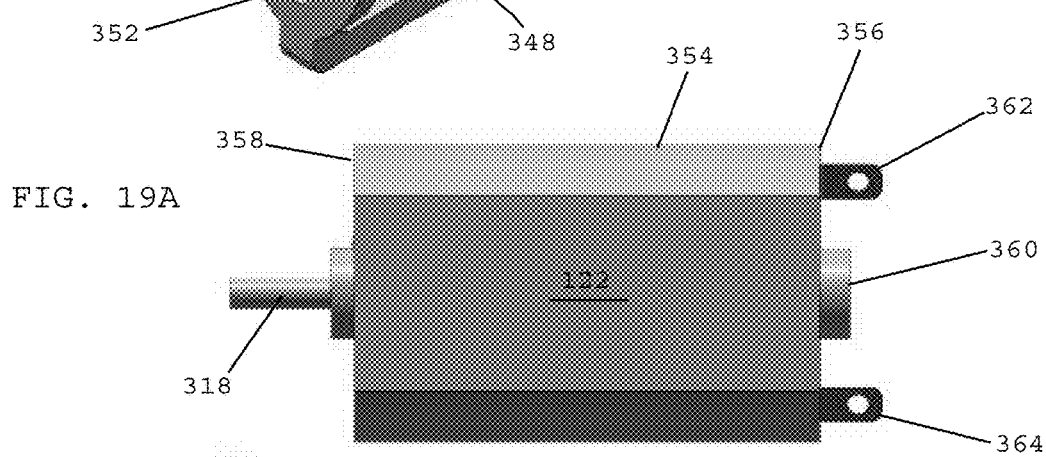
FIGS. 19A and 19B show a motor of a bipolar medical device for extracting tissue, in accordance with one embodiment of the present invention.
Figure 19B:
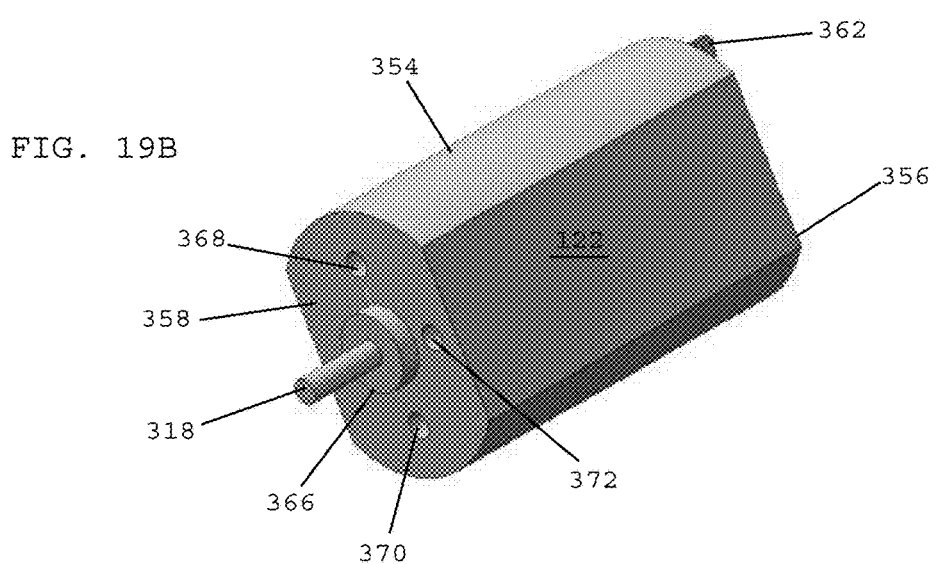

Referring to FIGS. 18 and 19A-19B, in one embodiment, the motor 122 preferably includes a motor housing 354 having a proximal end 356 and a distal end 358. The motor 122 includes a proximal central hub 360 adapted to be seated within the central opening 336 of the first plate 330 of the motor holder 124. The motor 122 desirably includes a first terminal 362 adapted to be positioned adjacent the first C-shaped opening 338 in the first plate 330 and a second terminal 364 adapted to be seated adjacent the second C-shaped opening 340 in the first plate 330. In one embodiment, one of the first and second terminals 362, 364 is adapted to be coupled with a positive terminal of a power source and the other one of the first and second terminals is adapted to be coupled with a negative terminal of a power source.

The motor 122 desirably includes the distal end 128 having a distal central hub 366 and the drive shaft 318 projecting from the distal central hub 366. The distal end 358 of the motor housing 354 includes motor fastener openings 368, 370 and 372. In one embodiment, the distal central hub 366 is inserted into the C-shaped opening 348 in the second plate 332 of the motor holder 124 so that the drive shaft 318 preferably projects beyond the distal face of the second plate 332. A first fastener (not shown) may be passed through the first fastener opening 350 in the second plate 332 and into the first fastener opening 368 in the distal face 358 of the motor housing 354, and second fastener may be passed through the second fastener opening 352 in the second plate 332 and into the second fastener opening 370 in the distal face of the motor housing 354 for securing the motor 122 to the second plate 332.

In one embodiment, once the motor 122 is secured within the motor holder 124, the motor and the motor holder are adapted to slide simultaneously with one another, in distal and proximal directions, along the longitudinal axis A, of the bipolar medical device 100 (FIG. 2).

Figure 20A:
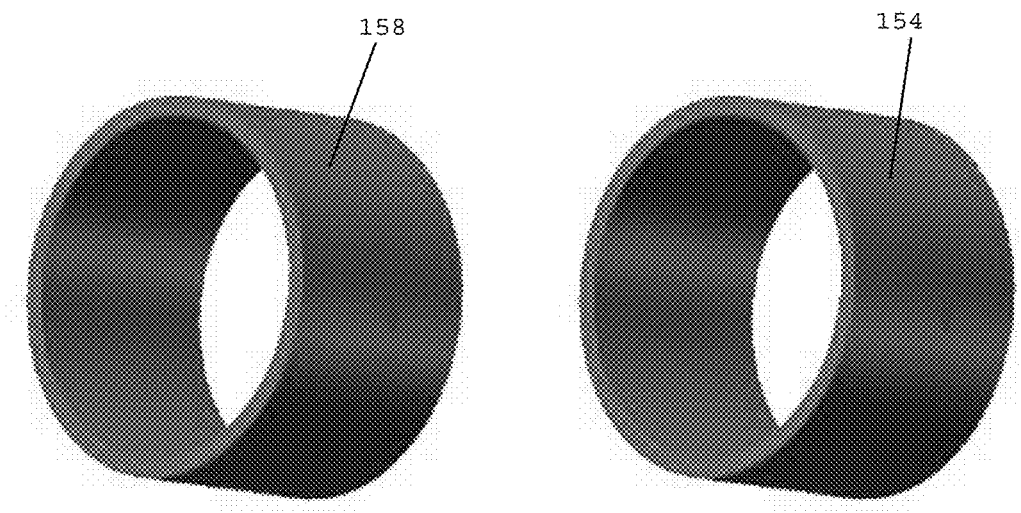
FIG. 20A shows first and second electrical bushings of a bipolar medical device for extracting tissue, in accordance with one embodiment of the present invention.
Figure 20B:
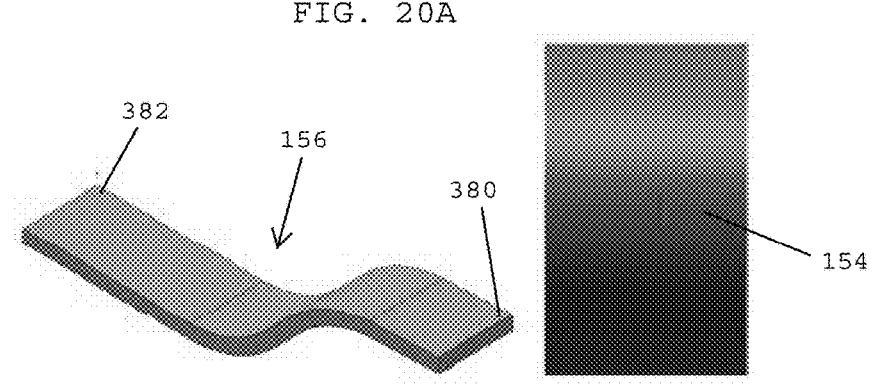
FIG. 20B shows a first electrical connector and the first electrical bushing of FIG. 20A, in accordance with one embodiment of the present invention.

Referring to FIGS. 2 and 20A-20C, in one embodiment, the bipolar medical device for extracting tissue desirably includes first and second bushings 154, 158 for connecting the first and second cutting elements 112, 114 with an electrosurgical generator. Referring to FIG. 20A, the first and second bushings 154, 158 are preferably ring-shaped and are preferably formed of a conductive material such as metal. Referring to FIG. 20B, the first bushing 154 is preferably electrically interconnected with the first tong extension 128 via a first electrical connector 156. The first electrical connector 156 preferably has a proximal end 380 that is adapted to slide over and engage an inner surface of the first bushing 154, and a distal end 382 that is permanently connected with a proximal end of the first tong extension 128, such as by being welded to the first tong extension.

Figure 20C:
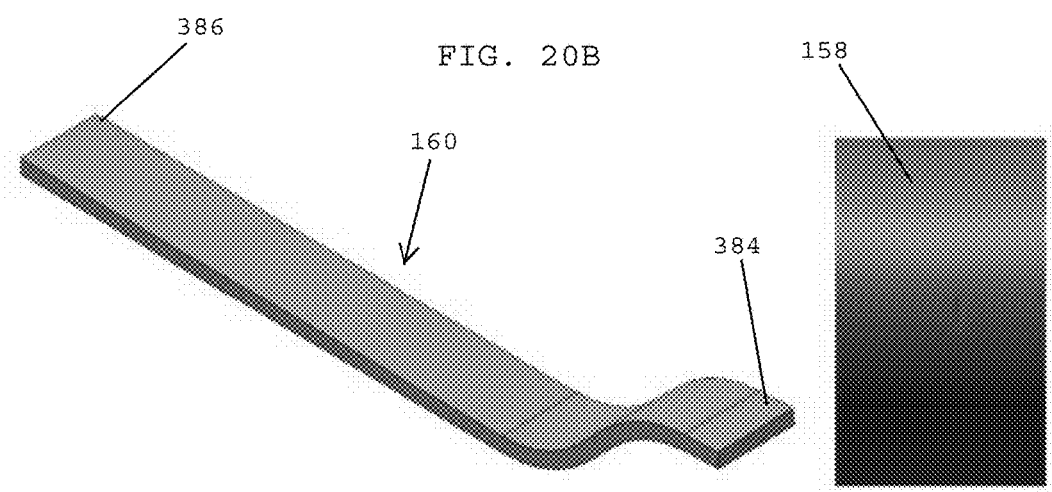
FIG. 20C shows a second electrical connector and the second electrical bushing of FIG. 20A, in accordance with one embodiment of the present invention.

Referring to FIG. 20C, the bipolar medical device preferably includes a second electrical connector 160 that forms an electrical interconnection between the second bushing 158 and the second tong extension 130 (FIG. 2). The second electrical connector 160 desirably includes a proximal end 384 adapted to slide over and engage the interior surface of the second bushing 158 and a distal end 386 that is permanently connected with a proximal end of the second tong extension 130, such as by being welded to the second tong extension.

Figure 21:
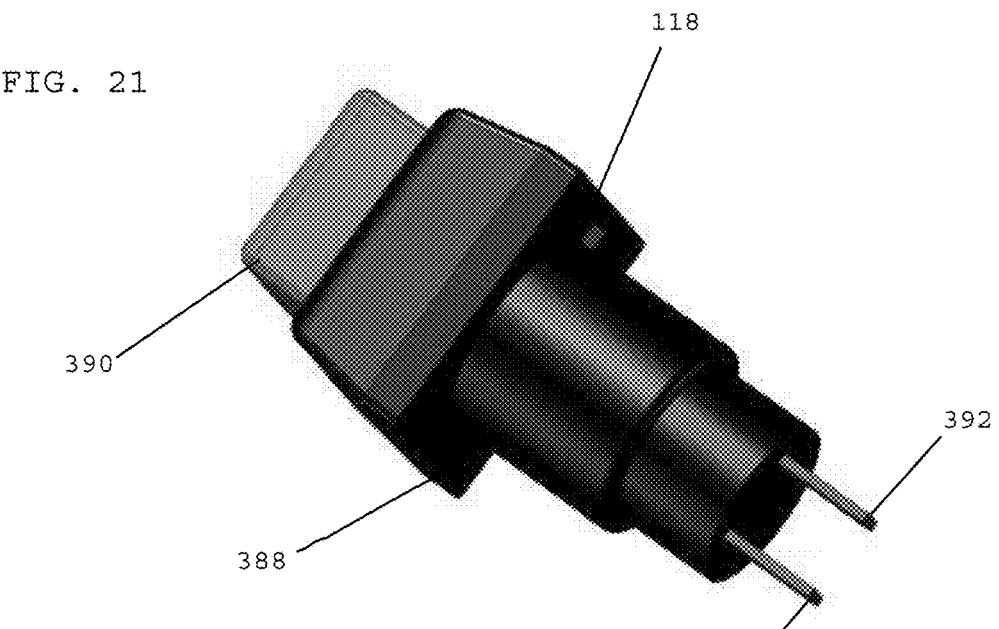
FIG. 21 shows a perspective view of a motor actuator momentary switch of a bipolar medical device for extracting tissue, in accordance with one embodiment of the present invention.

Referring to FIG. 21, in one embodiment, the motor actuator 118 (FIG. 2) preferably includes a base 388 adapted to be seated against an outer surface of the hand grip 108 section of the housing 106 (FIG. 1A). The motor actuator 118 also desirably includes a depressible button 390 that may be engaged for activating the motor for rotating the first and second cutting elements 112, 114. The motor actuator 118 desirably includes a first terminal 392 electrically interconnected with the second terminal 364 of the motor 122 (FIG. 19A) via a conductive conduit and a second terminal 394 electrically interconnected with one of the terminals of the power source 142 (FIG. 2).

Figure 22:
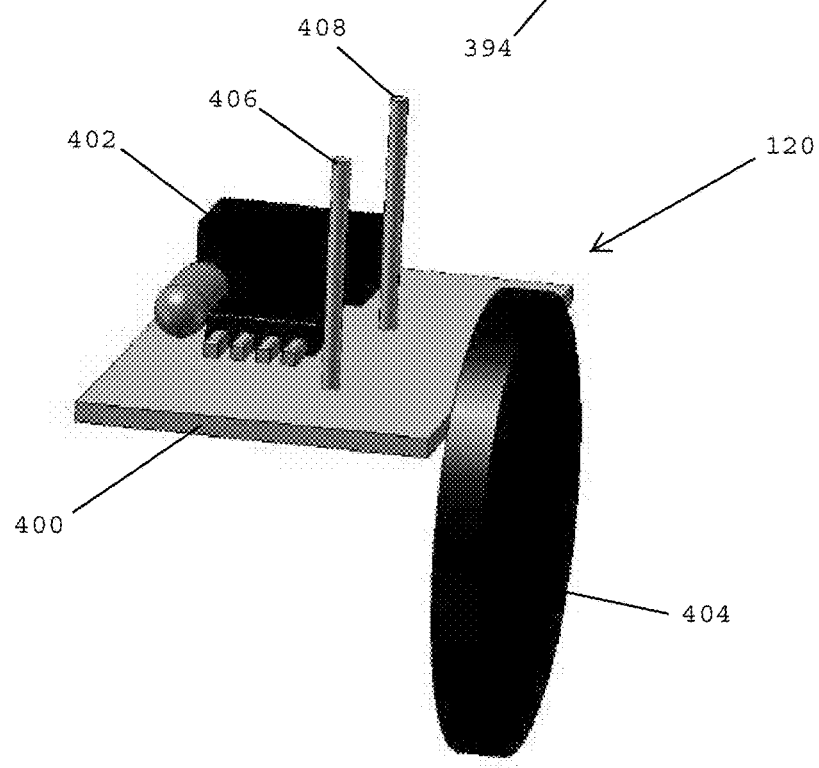
FIG. 22 shows a perspective view of a motor speed controller of a bipolar medical device for extracting tissue, in accordance with one embodiment of the present invention.

Referring to FIG. 22, in one embodiment, the bipolar medical device for extracting tissue preferably includes the motor speed adjuster 120. In one embodiment, the motor speed adjuster 120 preferably includes a printed circuit board 400 having one or more electrical components 402 mounted thereon. The one or more electrical components 402 may include a central processing unit, one or more microelectronic elements, memory chips, etc. The motor speed adjuster 120 also desirably includes a rotatable wheel 404 that may be rotated for adjusting the speed of the motor. The motor speed adjuster 120 desirably includes a first terminal 406 and a second terminal 408 adapted for being connected to an electrical circuit. In one embodiment, an operator may rotate the rotatable wheel 404 for adjusting the speed of rotation of the drive shaft 318 of the motor 122 (FIG. 19A).

Figure 23:
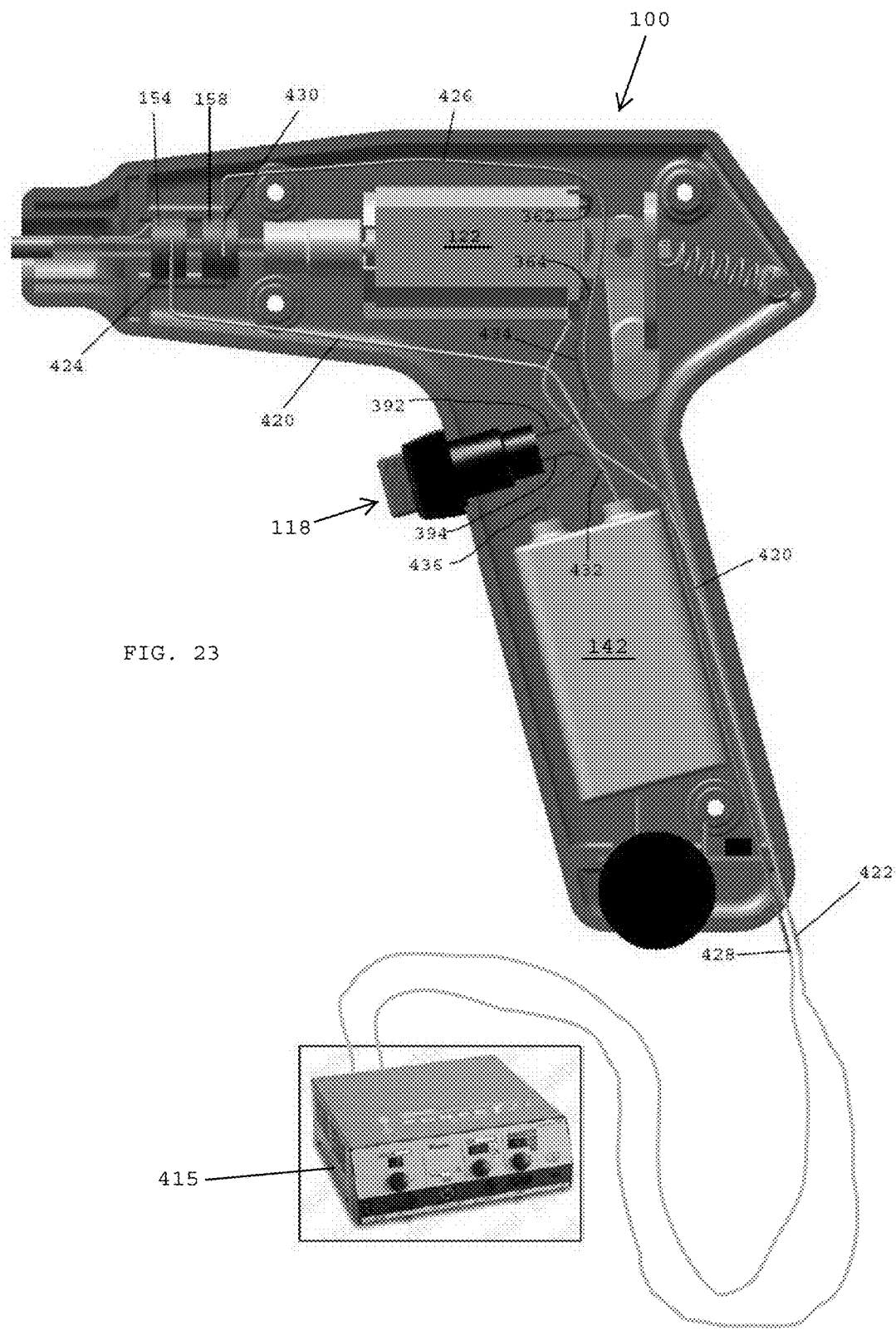
FIG. 23 shows a front elevational view of an electrical system of a bipolar medical device for extracting tissue, in accordance with one embodiment of the present invention.

Referring to FIG. 23, in one embodiment, the bipolar medical device 100 preferably includes a first electrical circuit for connecting the first and second cutting elements (FIG. 2) with an electrosurgical generator 415. In one embodiment, the first circuit preferably includes a first bushing wire 420 adapted to connect the first bushing 154 with a first pole (e.g., a positive pole) of the electrosurgical generator 415. The first bushing wire 420 preferably has a proximal end 422 connected with the electrosurgical generator 415 and a second end 424 connected with the first bushing 154. The first circuit desirably includes a second bushing wire 426 adapted to connect the second bushing 158 with a second pole (e.g., a negative pole) of the electrosurgical generator 415. The second bushing wire 426 desirably has a proximal end 428 connected with the electrosurgical generator 415 and a second end 430 connected with the second bushing 158. A positive charge is preferably passed through one of the bushing wires 420, 426 and a negative charge is preferably passed through the other bushing wire so that current flows from one of the cutting elements to the other cutting element for heating the tissue disposed between the first and second cutting elements.

The bipolar medical device 100 also preferably includes a second electrical circuit for energizing the motor 122 and rotating the first and second cutting elements. The second circuit preferably includes a first motor wire 432 that interconnects the first motor terminal 362 and a first terminal of the power source 142 and a second motor wire 434 that interconnects the second motor terminal 364 and the first terminal 392 of the motor actuator 118. The second circuit is completed by a battery wire 436 that interconnects the second terminal 394 of the motor actuator 118 with a second terminal of the power source 118. When the motor actuator 118 is engaged, the second circuit is closed for providing power to the motor 122 for rotating the drive shaft of the motor, which, in turn, rotates the first and second cutting elements of the split cutting tube for cutting tissue.

Figure 24A:
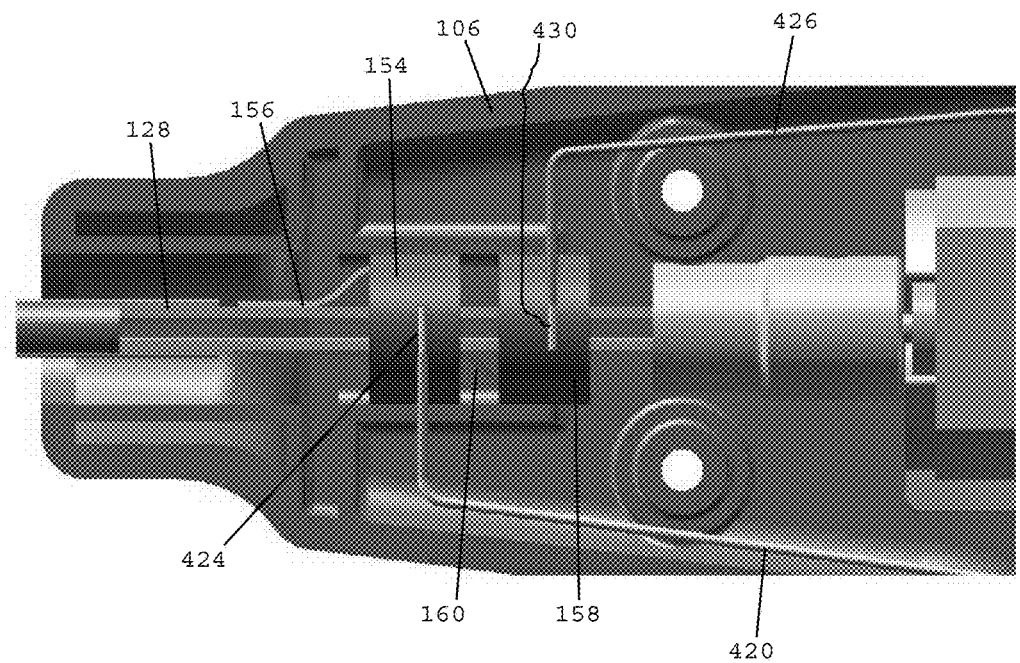
FIG. 24A shows a front elevational view of a portion of a bipolar medical device for extracting tissue, in accordance with one embodiment of the present invention.
Figure 24B:
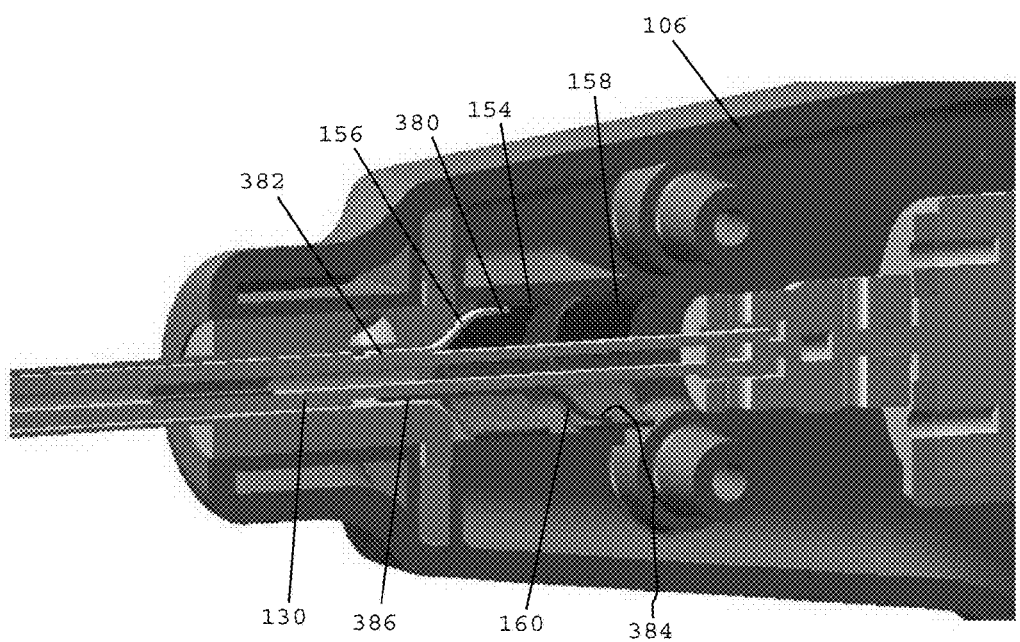
FIG. 24B shows a cross-sectional view of the portion of the bipolar medical device for extracting tissue of FIG. 24A.

Referring to FIGS. 24A and 24B, in one embodiment, the second end 424 of the first bushing wire 420 is in contact with the first bushing 154 for providing a positive charge to the first bushing 154, which is held in a stationary position within the device housing 106. The first electrical connector 156 forms a conductive path between the first bushing 154 and the first tong extension 128. The first electrical conductor 156 has a distal end 382 that is permanently affixed to the first tong extension 128 and a proximal end 380 adapted to slide over an annular inner surface of the first bushing 154 for maintaining an electrical connection between the first bushing 154 and the first tong extension 128. In one embodiment, the second end 430 of the second bushing wire 426 is in contact with the second bushing 158 for providing a negative charge to the second bushing 158, which is held in a stationary position within the device housing 106. The second electrical connector 160 forms a conductive path between the second bushing 158 and the second tong extension 130. The second electrical conductor 160 has a distal end 386 that is permanently affixed to the second tong extension 130 and a proximal end 384 adapted to slide over an annular inner surface of the second bushing 158 for maintaining an electrical connection between the second bushing 158 and the second tong extension 130.

Figure 25:
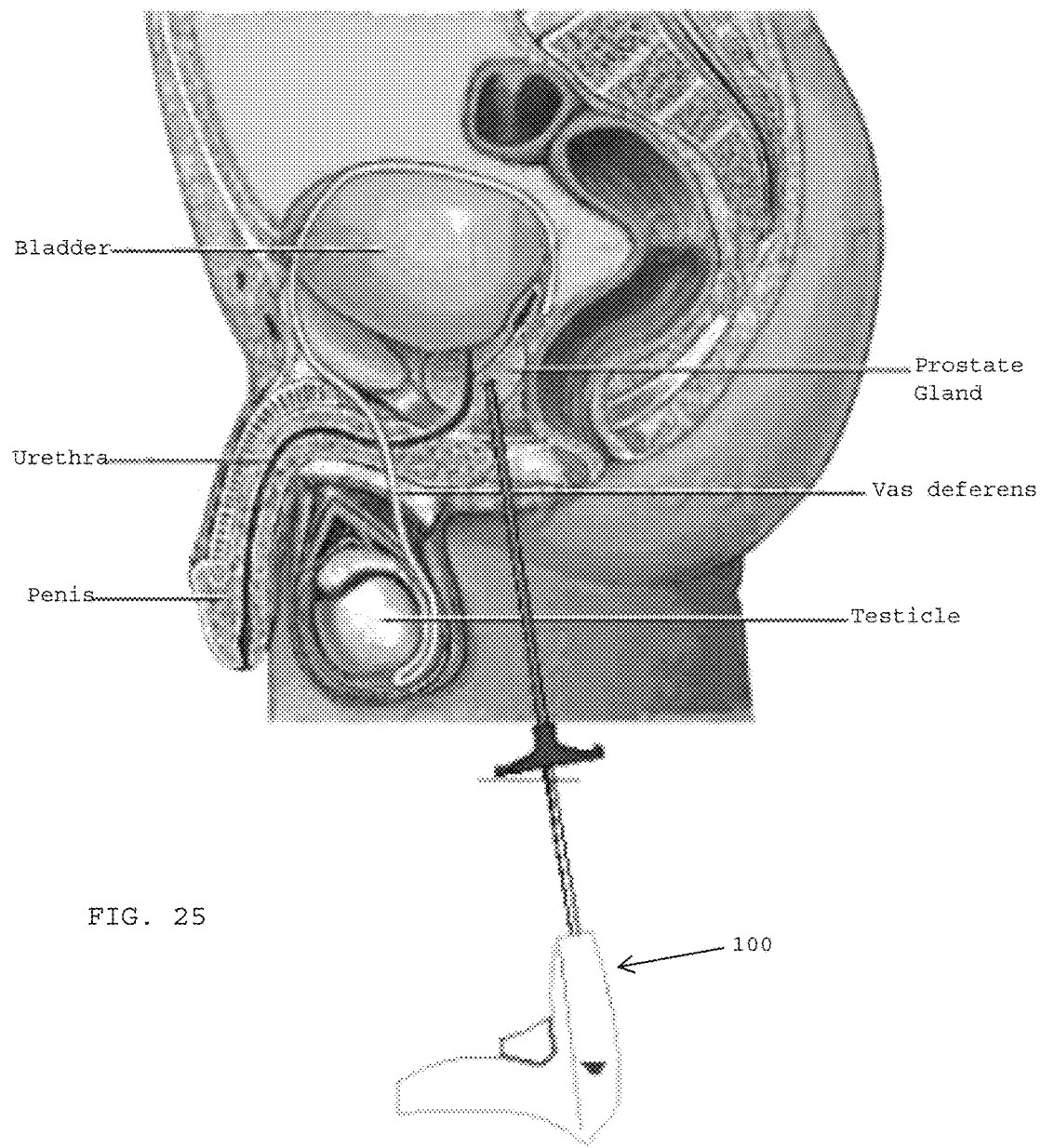
FIG. 25 shows a method of extracting tissue from a patient's prostate gland using a bipolar medical device for extracting tissue, in accordance with one embodiment of the present invention.

Referring to FIG. 25, in one embodiment, the bipolar medical device 100 for extracting tissue may be used to remove tissue such as prostate tissue. Although certain embodiments of the present invention disclose that the medical device may be used for removing prostate tissue, the medical device may be used for other applications including general surgery and gynecology. For example, the medical device disclosed herein may be used for removing fibroids in a uterus.

Figure 26:
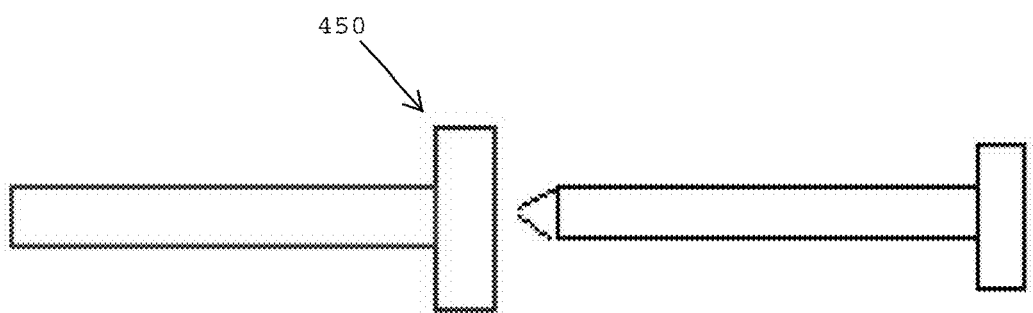
FIG. 26 shows a surgical tool for forming an incision during a method of extracting and cauterizing tissue, in accordance with one embodiment of the present invention.
Figure 27:
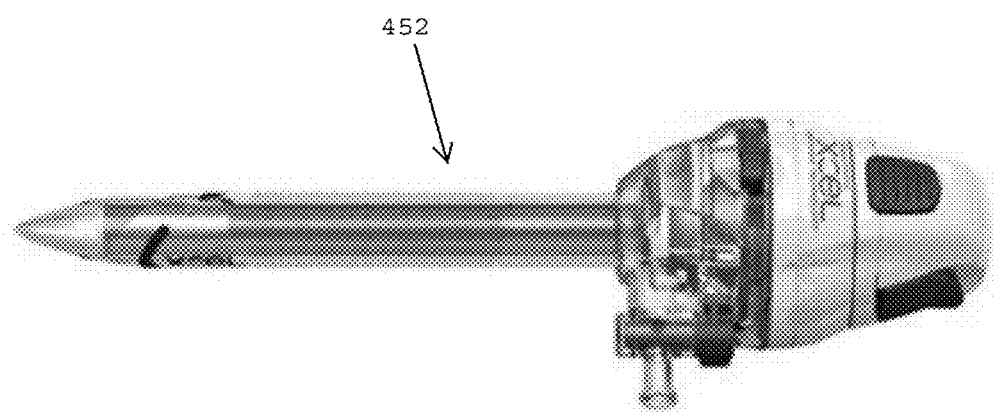
FIG. 27 shows a surgical tool for forming an incision during a method of extracting and cauterizing tissue, in accordance with one embodiment of the present invention.

Referring to FIGS. 25 and 26, in one embodiment, an introducer sheath tool kit 450 may be used for providing access to the prostate tissue. Referring to FIG. 27, in one embodiment, a trocar 452 such as a trocar sold under the trademark ENDOPATH XCEL by Ethicon, Inc., may be used for providing access to the prostate tissue. In one embodiment, an introducer sheath is used to gain access to the prostate in a transperineal fashion (i.e., between the scrotum and the rectum). The introducer sheath tool kit 450 and/or the trocar 452 preferably gently move aside internal viscera as they enter the body so that after the initial incision there is no further cutting, just a gentle separation of the tissue, which may be reunited at the end of the procedure. Once the trocar 452 and/or sheath tool kit 450 is removed, a hollow sheath or cannula preferably remains in place for providing a path for the bipolar medical device 100 to access the prostate tissue.

Figure 28A:
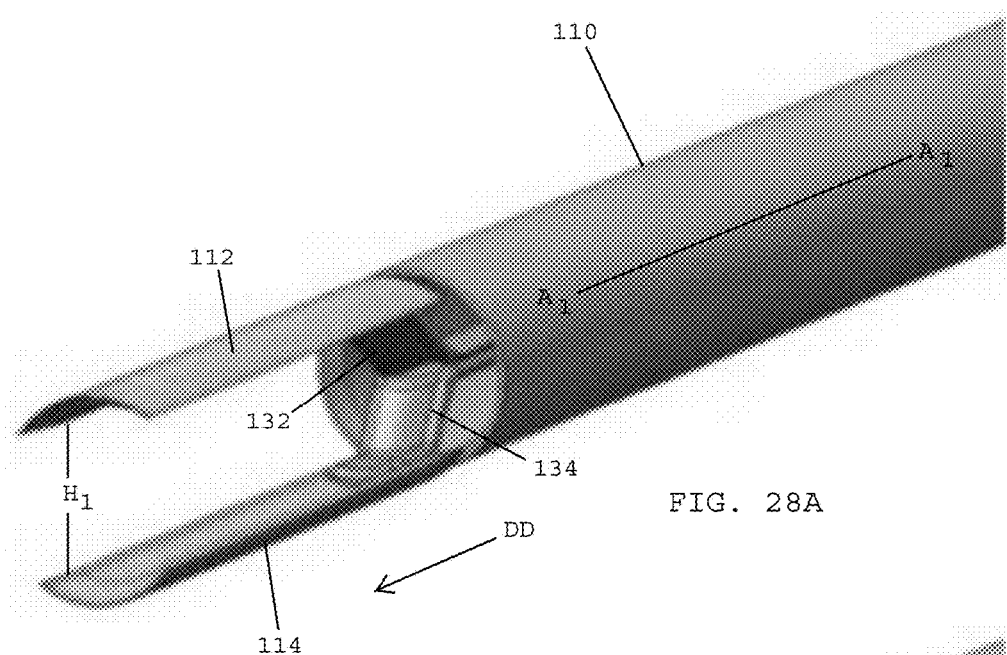
FIG. 28A shows a distal end of a bipolar medical device for extracting tissue with first and second cutting tubes extending from a distal end of the device, in accordance with one embodiment of the present invention.
Figure 28B:
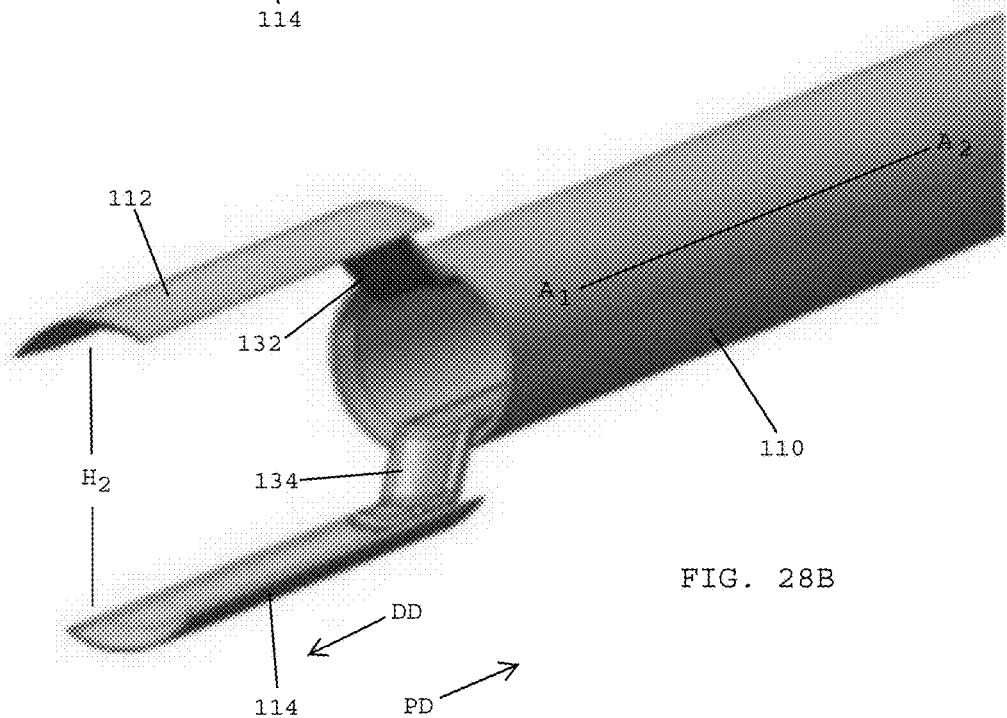
FIG. 28B shows the bipolar medical device of FIG. 28A with the first and second cutting tubes further extended from the position shown in FIG. 28A.

Referring to FIG. 28A, in one embodiment, the first and second cutting elements 112, 114 are spaced from one another a distance $H_1$ as the cutting elements are advanced through a laparoscopic instrument toward a tissue extraction site. Holding the cutting elements 112, 114 relatively close together during insertion minimizes tissue trauma. Referring to FIGS. 16 and 28B, upon reaching the tissue extraction site, the first and second thumb levers 146, 148 may be pressed toward the distal end 104 of the device 100 for advancing the first and second cutting elements 112, 114 distally in the distal direction DD. As the cutting elements move in the distal direction DD, the cutting elements advance from the distal end 262 of the outer tube 110. When the cutting elements and the tongs 132, 134 are beyond the distal end of the outer tube, the tongs 132, 134 are adapted to bias the first and second cutting elements 112, 114 away from one another for increasing the distance $H_2$ between the first and second cutting elements. The first and second cutting elements 112, 114 may be rotated about the longitudinal axis $A_1$ for cutting tissue. The electrosurgical generator 415 (FIG. 23) may be activated for passing an electric current between the first and second cutting elements 112, 114 for heating the tissue between the cutting elements. The thumb levers 146, 148 (FIG. 16) may be released so that the cutting elements may be retracted toward the proximal end of the device 100. As the cutting elements 112, 114 move in the proximal direction PD, the tongs 132, 134 and first and second cutting elements 112, 114 are forced toward one another for reducing the distance between the first and second cutting elements. In one embodiment, the first distance $H_1$ is about 3 mm and the second distance $H_2$ is about 5 mm.

Figure 29:
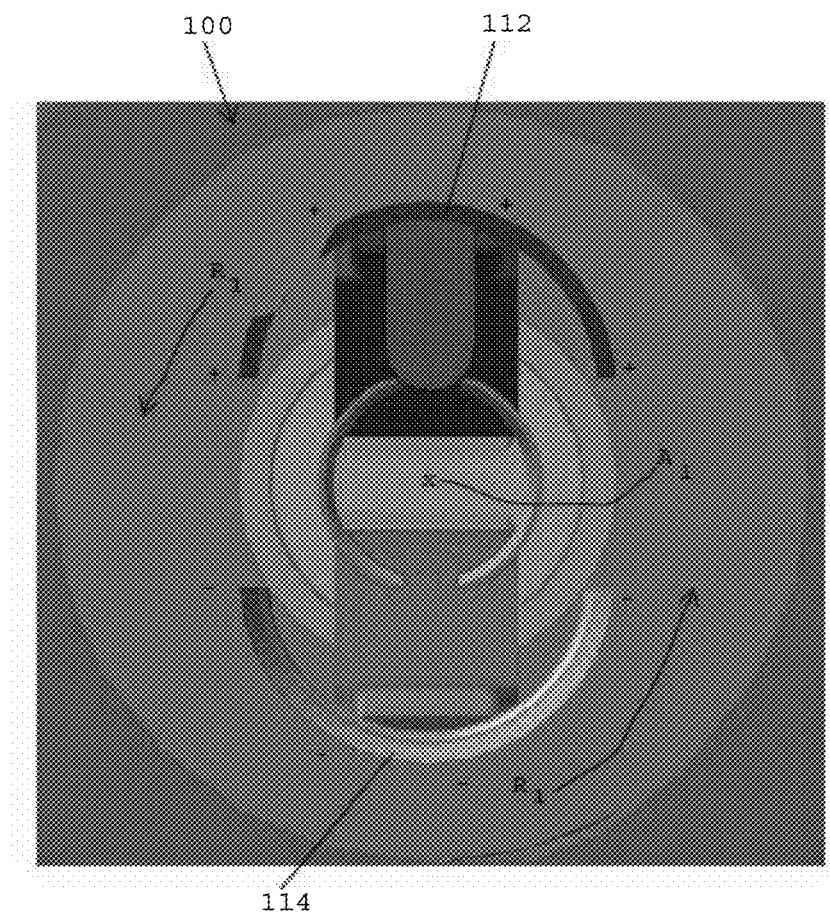
FIG. 29 shows a distal end view of a bipolar medical device for extracting tissue including first and second cutting elements of a split cutting tube, in accordance with one embodiment of the present invention.

FIG. 29 shows a distal end view of the bipolar medical device 100 for extracting tissue with the first and second cutting elements 112, 114 spaced from one another as shown in FIG. 28B. In one embodiment, the motor actuator 118 (FIG. 2) may be depressed for activating the motor and rotating the first and second cutting elements 112, 114 in a counterclockwise direction $R_1$ about the longitudinal axis $A_1$. As the cutting elements 112, 114 rotate, the distal cutting edges of the cutting elements may be advanced into tissue for cutting the tissue. At the same time, the first cutting element 112 may be positively charged (+) and the second cutting element 114 may be negatively charged (−) by the electrosurgical generator for minimizing bleeding of the tissue. In one embodiment, the medical device 100 may be used solely for removing tissue for biopsies without applying electrical current through the first and second cutting elements. In this embodiment, the medical device 100 may be re-introduced to cauterize tissue to control bleeding and/or continue tissue extraction.

Figure 30:
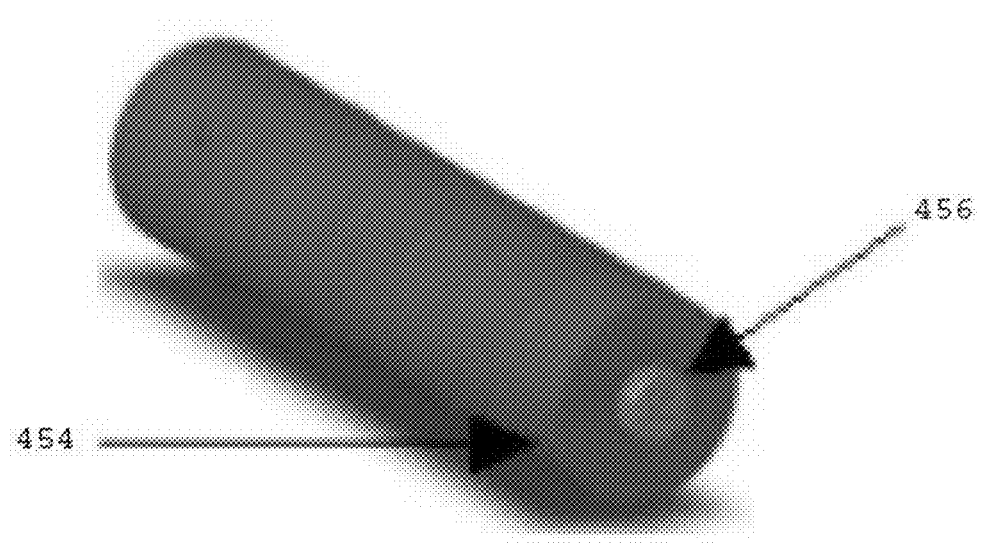
FIG. 30 shows a perspective distal end view of a tissue plug removed from a patient using a bipolar medical device for extracting tissue, in accordance with one embodiment of the present invention.

FIG. 30 shows a tissue core sample 454 that may be removed from a patient using the bipolar medical device disclosed herein. The cutting tooth 196 at the distal end of the first cutting element 112 (FIG. 7D) preferably provides a mechanism for engaging a distal end 456 of the tissue core sample 454 as the split cutting tube is used for removing the tissue core sample 454 from the patient. In one embodiment, the device forms the nub 456 at the distal end of the tissue core sample 454. The reduced cross section of the distal end nub 456 enables the tissue core sample 454 to be sheared off when the device is retracted so that the tissue core sample can be removed from the patient. The cutting tooth 196 on one of the first and second cutting elements (FIG. 7D) may function as a rake to pull the tissue out. In one embodiment, the thumb levers 146, 148 (FIG. 16) may be engaged to open the cutting elements to provide for removal of the tissue core sample 454.

Referring to FIG. 31, in one embodiment, a bipolar medical device 100' for extracting tissue preferably includes an extendable outer tube 110' and first and second cutting elements 112', 114' that may protrude from a distal end of the outer tube 110' for simultaneously cutting and/or cauterizing tissue. The outer tube 110' extends along a first longitudinal axis $A_2$ that is offset from a second longitudinal $A_3$ of a motor 122'. The motor 122' is preferably coupled with the first and second cutting elements 112', 114' via one or more gears and/or belts for selectively rotating the first and second cutting elements 112', 114' about the longitudinal axis $A_2$.

In one embodiment, the bipolar medical device 100' of FIG. 31 may be used for the continuous extraction of tissue such as being used during a laparoscopic procedure or a vaginal hysterectomy procedure. In one embodiment, the first and second cutting elements 112', 114' do not separate from one another as described herein for the embodiment shown in FIGS. 28A and 28B. In one embodiment, the outer tube 110' has an internal diameter of about 15-20 mm.

Referring to FIGS. 31 and 32, the outer tube 110' desirably has an elongated conduit extending from a proximal end to a distal end thereof so that a tissue grasping instrument 460 may be passed through the elongated conduit for grasping and removing cut tissue adjacent the first and second cutting elements 112', 114'. The bipolar medical device 100' shown in FIGS. 31 and 32 preferably includes one or more features of the bipolar medical device 100 shown and described above. In one embodiment, the first cutting element 112' may be positively charged and the second cutting element 114' may be negatively charged by an electrosurgical generator for minimizing bleeding of the cut tissue.

Figure 33:
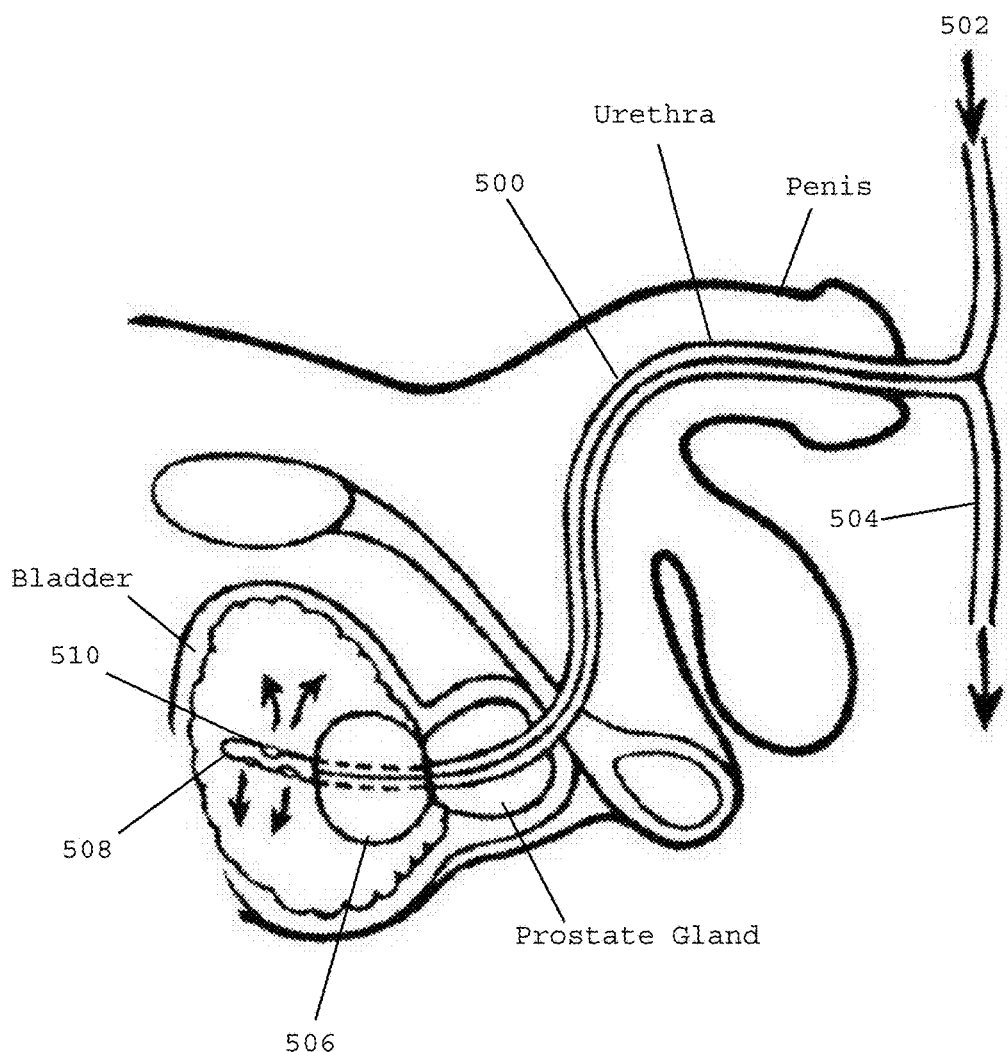
FIG. 33 shows a catheter used to introduce a cooling fluid during a tissue extraction procedure, in accordance with one embodiment of the present invention.

Referring to FIG. 33, in one embodiment, bipolar thermotherapy may be used to heat the inside of the prostate to destroy hyperplastic prostate tissue. In one embodiment, a multi-lumen Foley catheter 500 may be used for circulating cooling fluid through the urethra and bladder to prevent heat from damaging the wall of the urethra. The Foley catheter 500 preferably includes an inlet 502 for introducing cooling fluid into the bladder and an outlet 504 for draining fluid from the bladder and into a sterile bag. The Foley catheter 500 desirably includes a balloon for holding a distal end 508 of the catheter 500 in place within the bladder. The distal end 508 preferably has a plurality of openings 510 that enable the cooling fluid to be circulated through the bladder. In one embodiment, a temperature sensor may be inserted into a patient's rectum during the procedure to monitor the temperature so that the temperature outside the prostate does not get too high.

In one embodiment, the cutting tooth at the distal end of the first cutting element is angled at about 15 degrees to cut a spiral in tissue. The cutting tooth may be punched out from the body of the first cutting element or may be attached to the body of the first cutting element. Once the first cutting element has achieved a target depth, the operator may no longer desire to advance the device thereby creating a cutting plane and a tooth secures the tissue for extraction. In one embodiment, extraction of tissue is accomplished when the rotating first and second cutting elements are advanced. The first and second cutting elements may be ribbed and/or barbed to secure tissue for extraction. Once depth is achieved, the device is removed from the patient. The motor actuator may be actuated so that the distal ends of the first and second cutting elements open to release the tissue.

In one embodiment, the first and second cutting elements of the slit cutting tube may separate from each other after insertion into tissue and before rotating the first and second cutting elements. This methodology enables the device to reach the target tissue with less trauma. For example, the first and second cutting elements may be inserted into the tissue at a 3 mm gap and may then be opened to a 5 mm gap. When the distal tip of the device reaches the target tissue, the split tube halves may be opened to a 5 mm gap and the instrument advanced for cutting, coring and coagulating tissue. Upon reaching appropriate depth, the first and second cutting elements may contract on the target tissue for capturing the tissue in the closed tubular cutting halves. The two split tube halves may have features such as protrusions to aid in securing the cut tissue.

The present invention provides a number of benefits over prior art devices and methods. First, the present invention eliminates the need for using a catheter after the procedure for voiding. The present invention also provides a method that is minimally invasive, and that does not require excessive capital expenditures for equipment. The present invention may also be performed by medical personnel in an office setting, an ambulatory center or a surgical suite.

In one embodiment, the cauterizing step controls bleeding. The remaining tissue is necrosed and will be absorbed by the body. In the case of BPH, this further reduces the prostate size.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A bipolar medical device for extracting tissue comprising:

an outer tube extending along a longitudinal axis;

a split tube disposed within said outer tube, said split tube having a distal end including a first cutting element located at a distal-most end of said split tube, said first cutting element having a distal cutting surface at the distal-most end of said split tube and an opposing second cutting element located at the distal-most end of said split tube, said second cutting element having a distal cutting edge at the distal-most end of said split tube, said distal cutting surface and said distal cutting edge being adapted for cutting tissue, wherein said split tube is rotatable about the longitudinal axis of said outer tube and relative to said outer tube;

said first cutting element comprising a first semi-tubular body having a concave inner surface that extends to the distal-most end of said first cutting element, and said second cutting element comprising a second semi-tubular body having a concave inner surface that extends to the distal-most end of said second cutting element;

said split tube being axially moveable relative to said outer tube for advancing said first and second cutting elements beyond a distal end of said outer tube, wherein the distance between said first and second cutting elements changes when said first and second cutting elements are advanced distally beyond said distal end of said outer tube;

an electrosurgical generator coupled with said split tube, wherein said first cutting element is connected with a first pole of said electrosurgical generator and said second element is connected with a second pole said electrosurgical generator, wherein said first and second cutting elements connected with said electrosurgical generator are normally biased away from one another so that the distance between said first and second cutting elements is greater when said first and second cutting elements are extended distally beyond said distal end of said outer tube and smaller when said first and second cutting elements are retracted into said outer tube;

wherein said split tube includes a first tong having a distal end connected with said first cutting element and a second tong having a distal end connected with said second cutting element;

a first conductive bushing electrically connected with the first pole of said electrosurgical generator;

a first electrical connector having a distal end permanently connected with a proximal end of said first tong and a proximal end that is configured to slide over a surface of said first bushing for maintaining an electrical connection between said first tong and said first bushing as said split tube rotates and moves axially relative to said outer tube;

a second conductive bushing electrically connected with the second pole of said electrosurgical generator; and a second electrical connector having a distal end permanently connected with a proximal end of said second tong and a proximal end that is configured to slide over a surface of said second bushing for maintaining an electrical connection between said second tong and said second bushing as said split tube rotates and moves axially relative to said outer tube.

2. The medical device as claimed in claim 1, wherein said electrosurgical generator is adapted to generate an electric current that flows between said first and second cutting elements for heating tissue located adjacent said first and second cutting elements.

3. The medical device as claimed in claim 1, wherein the longitudinal axis extends between proximal and distal ends of said outer tube, and said split tube is axially moveable along the longitudinal axis relative to said outer tube.

4. The medical device as claimed in claim 3, further comprising:
   a housing connected to said proximal end of said outer tube;
   a motor disposed within said housing and being coupled with said split tube;
   a power source coupled with said motor;
   a motor actuator coupled with said motor for selectively activating said motor for rotating said split tube about the longitudinal axis.

5. The medical device as claimed in claim 4, further comprising a lever assembly mounted on said housing and being coupled with said motor and said split tube, wherein said lever assembly is engageable for simultaneously advancing said motor and said split tube toward said distal end of said outer tube.

6. The medical device as claimed in claim 4, wherein said motor is slideably mounted within said housing for sliding toward and away from said distal end of said outer tube.

7. The medical device as claimed in claim 1, wherein said first and second cutting elements are electrically isolated from one another.

8. The medical device as claimed in claim 1, wherein said outer tube has an outer diameter, wherein the distance between said first and second cutting elements is greater than the outer diameter of said outer tube when said first and second cutting elements are extended distally beyond said distal end of said outer tube and is smaller than the outer diameter of said outer tube when said first and second cutting elements are retracted into said outer tube.

9. The medical device as claimed in claim 1, wherein said first semi-tubular body comprises a convex outer surface that extends to the distal-most end of said first cutting element, and said second semi-tubular body comprising a convex outer surface that faces away from said first cutting element and that extends to the distal-most end of said second cutting element.

10. The medical device as claimed in claim 1, wherein said first cutting element comprises a tooth projecting radially inward toward said opposing second cutting element.

11. The medical device as claimed in claim 10, wherein said tooth is located adjacent and proximal to said distal cutting surface at the distal-most end of said first cutting element.

12. The medical device as claimed in claim 11, wherein said tooth includes a leading edge having a sharpened cutting surface that lies within a plane that defines an angle with said first distal cutting surface at the distal-most end of said first cutting element.

13. The medical device as claimed in claim 12, wherein during rotation of said first and second cutting elements about the longitudinal axis said tooth is adapted to cut tissue, and wherein said tooth is adapted to abut against an end of the cut tissue for removing the cut tissue from a tissue extraction site.

14. The medical device as claimed in claim 1, further comprising a catheter adapted for supplying a cooling liquid to a patient's bladder during a tissue extraction procedure for protecting the patient's tissue from thermal damage.

15. The medical device as claimed in claim 1, said first cutting element further comprising:
   a first angled cutting surface extending proximally from a first end of said distal cutting surface at said distal-most end of said first cutting element; and
   a second angled cutting surface extending proximally from a second end of said distal cutting surface at said distal-most end of said first cutting element.

16. A bipolar medical device for extracting tissue comprising:
   a housing;
   an outer tube projecting from said housing, said outer tube extending along a longitudinal axis and including a proximal end connected with said housing and a distal end spaced from said proximal end;
   a split tube disposed within said outer tube, said split tube having a distal end including a first cutting element located at a distal-most end of said split tube, said first cutting element having a distal-most end with a distal cutting surface at said distal-most end of said split tube and an opposing second cutting element located at said distal-most end of said split tube, said second cutting element having a distal-most end with a distal cutting edge at said distal-most end of said of said second cutting element;
   said first cutting element comprising a first semi-tubular body having a concave inner surface that extends to said distal-most end of said first cutting element and said distal-most end of said split tube, and said second cutting element comprising a second semi-tubular body having a concave inner surface that extends to said distal-most end of said second cutting element and said distal-most end of said split tube;
   said split tube being axially moveable relative to said outer tube for advancing said first and second cutting elements beyond said distal end of said outer tube, wherein the distance between said first and second cutting elements is greater when said first and second cutting elements are advanced distally beyond said distal end of said outer tube and is smaller when said first and second cutting elements are retracted to be proximal to said distal end of said outer tube;
a motor coupled with said split tube for selectively rotating said split tube and said first and second cutting elements about the longitudinal axis;
an electrosurgical generator coupled with said split tube, wherein said first cutting element is connectable with a first pole of said electrosurgical generator and said second element is connectable with a second pole said electrosurgical generator, wherein said electrosurgical generator generates an electric current that flows between said first and second cutting elements for heating tissue located adjacent said first and second cutting elements, and wherein said first and second cutting elements are biased away from one another;
wherein said split tube includes a first tong having a distal end connected with said first cutting element and a second tong having a distal end connected with said second cutting element;
a first conductive bushing electrically connected with the first pole of said electrosurgical generator;
a first electrical connector having a distal end permanently connected with a proximal end of said first tong and a proximal end that is configured to slide over a surface of said first bushing for maintaining an electrical connection between said first tong and said first bushing as said split tube rotates about the longitudinal axis and moves axially relative to said outer tube;
a second conductive bushing electrically connected with the second pole of said electrosurgical generator; and
a second electrical connector having a distal end permanently connected with a proximal end of said second tong and a proximal end that is configured to slide over a surface of said second bushing for maintaining an electrical connection between said second tong and said second bushing as said split tube rotates about the longitudinal axis and moves axially relative to said outer tube.

17. The medical device as claimed in claim 16, wherein said motor is adapted to rotate said first and second cutting elements about the longitudinal axis for cutting tissue.

18. The medical device as claimed in claim 16, wherein the distance between said first and second cutting elements is greater than an outer diameter of said outer tube when in the extended position.

19. The medical device as claimed in claim 18, further comprising a lever assembly coupled with said motor and said split tube for simultaneously advancing said motor and said first and second cutting elements toward said distal end of said outer tube.

20. The medical device as claimed in claim 16, wherein said first and second tongs extend through said outer tube and are coupled with a drive shaft of said motor, said first and second tongs being electrically isolated from one another.

21. The medical device as claimed in claim 16, wherein said first semi-tubular body comprises a convex outer surface that extends to said distal-most end of said first cutting element, and said second semi-tubular body having a convex outer surface that faces away from said first cutting element and that extends to said distal-most end of said second cutting element.

22. The medical device as claimed in claim 16, further comprising:
said outer tube including an elongated conduit extending from said proximal end to said distal end thereof; and
a tissue grasping tool passable through the elongated conduit for grasping tissue cut by said first and second cutting elements at said distal end of said outer tube.

23. A bipolar medical device for extracting tissue comprising:
an outer tube extending along a longitudinal axis, said outer tube having an outer diameter;
a split tube disposed within said outer tube, said split tube having a distal end including a first cutting element located at a distal-most end of said split tube, said first cutting element having a distal-most end with a distal cutting surface at said distal-most end of said split tube and an opposing second cutting element located at said distal-most end of said split tube, said second cutting element having a distal-most end with a distal cutting edge at said distal-most end of said split tube, said distal cutting surface and said distal cutting edge being adapted for cutting tissue;
said first cutting element comprising a first semi-tubular body having a concave inner surface that extends to said distal-most end of said first cutting element, and said second cutting element comprising a second semi-tubular body having a concave inner surface that opposes said concave inner surface of said first cutting element and that extends to said distal-most end of said second cutting element;
said split tube being axially moveable along the longitudinal axis of said outer tube for advancing said first and second cutting elements beyond a distal end of said outer tube, wherein when said first and second cutting elements are advanced distally beyond said distal end of said outer tube the distance between said first and second cutting elements is greater than the outer diameter of said outer tube;
an electrosurgical generator coupled with said split tube, wherein said first cutting element is connected with a first pole of said electrosurgical generator and said second element is connected with a second pole said electrosurgical generator;
a motor coupled with said split tube for selectively rotating said split tube and said first and second cutting elements about the longitudinal axis;
wherein said split tube includes a first tong having a distal end connected with said first cutting element and a second tong having a distal end connected with said second cutting element;
a first conductive bushing electrically connected with the first pole of said electrosurgical generator;
a first electrical connector having a distal end permanently connected with a proximal end of said first tong and a proximal end that is configured to slide over a surface of said first bushing for maintaining an electrical connection between said first tong and said first bushing as said split tube rotates about and moves axially along the longitudinal axis of said outer tube;
a second conductive bushing electrically connected with the second pole of said electrosurgical generator; and
a second electrical connector having a distal end permanently connected with a proximal end of said second tong and a proximal end that is configured to slide over a surface of said second bushing for maintaining an electrical connection between said second tong and said second busing as said split tube rotates about and moves axially along the longitudinal axis of said outer tube.

24. The medical device as claimed in claim 23, wherein said first and second cutting elements connected with said electrosurgical generator are normally biased away from one another, and wherein the distance between said first and second cutting elements is greater when said first and second cutting elements are extended distally beyond said distal end of said outer tube and smaller when said first and second cutting elements are retracted into said outer tube.

* * * * *